(12) United States Patent
Hasegawa et al.

(10) Patent No.: US 7,947,697 B1
(45) Date of Patent: May 24, 2011

(54) 8-(3-PENTYLAMINO)-2-METHYL-3-(2-CHLORO-4-METHOXYPHENYL)-6,7-DIHYDRO-5H-CYCLOPENTA[D]PYRAZOLO[1,5-A]PYRIMIDINE METHANESULFONATE AS A CRF ANTAGONIST

(75) Inventors: Tomoyuki Hasegawa, Sakai-gun (JP); Toshiaki Matsui, Sakai-gun (JP); Hiroshi Araki, Sakai-gun (JP); Tetsuji Saito, Mishima-gun (JP); Tetsuo Obitsu, Mishima-gun (JP); Masaki Okamoto, Suita (JP); Yuichi Gemba, Sakai-gun (JP); Yutaka Mikami, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 417 days.

(21) Appl. No.: 10/561,214

(22) PCT Filed: Jun. 24, 2004

(86) PCT No.: PCT/JP2004/009263
§ 371 (c)(1),
(2), (4) Date: Aug. 29, 2006

(87) PCT Pub. No.: WO2004/113344
PCT Pub. Date: Dec. 29, 2004

(30) Foreign Application Priority Data

Jun. 25, 2003 (JP) ................. 2003-181908

(51) Int. Cl.
C07D 487/04 (2006.01)
A61K 31/519 (2006.01)
A61P 25/28 (2006.01)
A61P 25/24 (2006.01)
A61P 3/04 (2006.01)
A61P 25/22 (2006.01)

(52) U.S. Cl. ........................ 514/267; 544/252
(58) Field of Classification Search .............. 544/252; 514/267
See application file for complete search history.

(56) References Cited

U.S. PATENT DOCUMENTS

| 5,843,951 | A | 12/1998 | Inoue et al. |
| 6,194,574 | B1 | 2/2001 | Yoon |
| 6,348,466 | B1 | 2/2002 | Haddach et al. |
| 6,495,686 | B2 | 12/2002 | Yoon |
| 6,514,982 | B1 | 2/2003 | Haddach et al. |
| 6,531,475 | B1 | 3/2003 | Haddach et al. |
| 6,723,721 | B2 | 4/2004 | Haddach et al. |
| 7,034,153 | B2 * | 4/2006 | Nakai et al. ............. 544/249 |
| 2004/0072833 | A1 | 4/2004 | Nakai et al. |

FOREIGN PATENT DOCUMENTS

| EP | 0503099 A1 | 9/1992 |
| EP | 0795555 A1 | 9/1997 |
| EP | 1354884 A1 | 10/2003 |
| JP | 5-112571 A | 5/1993 |
| WO | WO 97/11946 A1 | 4/1997 |
| WO | 99/64422 | 12/1999 |
| WO | 00/27846 | 5/2000 |
| WO | 00/27850 | 5/2000 |
| WO | WO 02/053565 A1 | 7/2002 |

OTHER PUBLICATIONS

Berge et. al. (Journal of Pharmaceutical Sciences, 1977, pp. 1-19).*
Bastin et. al. (Organic Process & Development, 2000, 4, pp. 427-435).*
Jones et al, "British Society of Gastroenterology guidelines for the management of the irritable bowel syndrome." Gut 2000, (Suppl II)47:ii1-ii19).*
Palmer (TRENDS in Pharmacological Sciences 23(9) 426-433).*
International Search Report dated Sep. 21, 2004.
Leach, C. et al., "Reversible Inhibitors of the Gastric ($H^+/K^+$)-ATPase. 2.1-Arylpyrrolo[3,2-c]quinolines: Effect of the 4-Substituent", J. Med. Chem., 35(10), 1845-1852 (1992).
Sivakamasundari, S. et al., "Pyrroloquinolines: PartIV†-Synthesis of 1-Aryl-1H-pyrrolo[2,3-b]quinolines", Indian J. Chem., 26B(8), 744-747 (1987).
Smith, L et al., "A novel and highly efficient synthesis of the aza analogs of tacrine", Tetrahedron Letters, 40, 5643-5646 (1999).
Himbert, G. et al., "Cyclisierung von $N^1$, $N^2$-Diaryl-$N^1$-phenacyl-3-aminopropiolamidinen", Liebigs Ann. Chem. 1985, 1389-1397, abstract.
Tominaga, Y. et al, "Synthesis of Methylthiomaleimides for the Preparation of Pyridazines and Related Compounds", J. Heterocyclic Chem., 39(3), 571-591 (2002).

* cited by examiner

Primary Examiner — Susanna Moore
(74) Attorney, Agent, or Firm — Sughrue Mion, PLLC

(57) ABSTRACT

8-(3-pentylamino)-2-methyl-3-(2-chloro-4-methoxyphenyl)-6,7-dihydro-5H-cyclopenta[d]pyrazolo[1,5-a]pyrimidine methanesulfonate of the structural formula (I)

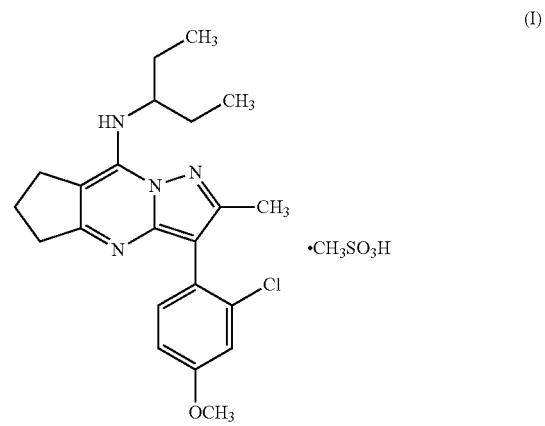

has Corticotropin Releasing Factor (CRF) antagonist activity and is useful in treating neuropsychiatric and digestive system diseases.

4 Claims, 6 Drawing Sheets

US 7,947,697 B1

8-(3-PENTYLAMINO)-2-METHYL-3-(2-CHLORO-4-METHOXYPHENYL)-6,7-DIHYDRO-5H-CYCLOPENTA[D]PYRAZOLO[1,5-A]PYRIMIDINE METHANESULFONATE AS A CRF ANTAGONIST

TECHNICAL FIELD

The present invention relates to 8-(3-pentylamino)-2-methyl-3-(2-chloro-4-methoxyphenyl)-6,7-dihydro-5H-cyclopenta[d]pyrazolo[1,5-a]pyrimidine methanesulfonate, a crystal thereof, a process for the preparation thereof, or a process for the preparation of an intermediate thereof.

BACKGROUND

Corticotropin Releasing Factor (CRF) was a peptide comprising 41 amino acid residues and isolated from ovine hypothalamic in 1981. It was suggested that CRF was released from hypothalamic and controlled a secretion of adrenocorticotropic hormone (ACTH) from hypophysis [*Science*, 218, 377-379 (1982)].

ACTH, which is released by a stimulation of CRF, stimulates a secretion of cortisol from adrenal cortex, and relates to a systemic action for reproduction, growth, gastrointestinal function, inflammation, immune system, nervous system etc. Consequently, CRF is believed to play a role as a regulator of these functions. In view of these, a relationship of CRF and a central nervous system disease or a neuropsychiatric disorder has gained a lot of attention.

In WO 02/053565, a compound of formula (A)

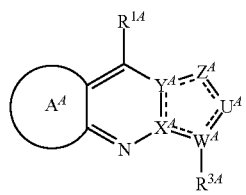

(A)

wherein $X^A$ and $Y^A$ each, independently, is carbon or nitrogen and both are not nitrogen at the same time; $W^A$ is carbon or nitrogen; $U^A$ and $Z^A$ each, independently, is $CR^{2A}$, $NR^{13A}$, nitrogen, oxygen, sulfur, C=O or C=S;

$R^{2A}$ is (i) hydrogen, (ii) C1-8 alkyl, (iii) C2-8 alkenyl, (iv) C2-8 alkynyl, (v) halogen atom, (vi) $CF_3$, (vii) cyano, (viii) nitro, (ix) $NR^{9A}R^{10A}$, (x) $OR^{11A}$, (xi) SH, (xii) $S(O)_{nA}R^{12A}$, (xiii) $COR^{11A}$, (xiv) $COOR^{11A}$, (xv) $CONR^{9A}R^{10A}$, (xvi) C3-10 mono- or bi-carbocyclic ring, (xvii) 3- to 10-membered mono- or bi-heterocyclic ring containing 1-4 of nitrogen(s), 1-2 of oxygen(s) and/or 1-2 of sulfur(s) or (xviii) substituted C1-4 alkyl;

═══ is a single bond or a double bond;

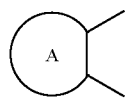

is C4-6 carbocyclic ring or 4-6 membered heterocyclic ring containing at least one of nitrogen, oxygen and sulfur and these rings are unsubstituted or substituted by 1-3 of substitutes selected from C1-4 alkyl, C1-4 alkoxy, halogen atom and $CF_3$;

$R^{1A}$ is (i) unsubstituted or substituted C1-8 alkyl, (ii) unsubstituted or substituted C2-8 alkenyl, (iii) unsubstituted or substituted C2-8 alkynyl, (iv) $NR^{4A}R^{5A}$, (v) $OR^{6A}$, (vi) SH, (vii) $S(O)_nR^{7A}$, (viii) $COR^{6A}$, (ix) $COOR^{6A}$, (x) $CONR^{4A}R^{5A}$, (xi) $NR^{8A}COR^{6aA}$, (xii) $NR^{8A}COOR^{6A}$, (xiii) $NR^{8A}CONR^{4A}R^{5A}$, (xiv) unsubstituted or substituted C3-15 mono- or bi-carbocyclic ring, (xv) unsubstituted or substituted 3-15 membered mono- or bi-heterocyclic ring containing 1-4 of nitrogen(s), 1-2 of oxygen(s) and/or 1-2 of sulfur(s);

was described as CRF receptor antagonist.

In addition, in WO 02/053565, 8-(3-pentylamino)-2-methyl-3-(2-chloro-4-methoxyphenyl)-6,7-dihydro-5H-cyclopenta[d]pyrazolo[1,5-a]pyrimidine hydrochloride was described.

As an intermediate of the compound of formula (A), a compound of formula (B) was described:

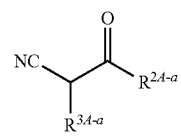

(B)

wherein $R^{2A-a}$ is (i) hydrogen, (ii) C1-8 alkyl, (iii) C2-8 alkenyl, (iv) C2-8 alkynyl, (v) halogen atom, (vi) trifluoromethyl, (vii) cyano, (viii) nitro, (ix) $NR^{9A}R^{10A}$, (x) $OR^{11A}$, (xi) SH, (xii) $S(O)nR^{12A}$, (xiii) $COR^{11A}$, (xiv) $COOR^{11A}$, (xv) $CONR^{9A}R^{10A}$, (xvi) C3-10 mono- or bi-carbocyclic ring, (xvii) 3- to 10-membered mono- or bi-heterocyclic ring containing 1-4 of nitrogen(s), 1-2 of oxygen(s) and/or 1-2 of sulfur(s) or (xviii) substituted C1-4 alkyl, with the proviso that $R^{2A-a}$ is not OH, cyano, =N—$OR^{11A}$, or a group containing OH, cyano or =N—$OR^{11A}$, $R^{3A-a}$ is (i) substituted C5-10 mono- or bi-carbocyclic ring, or (ii) substituted 5-10 membered mono- or bi-heterocyclic ring containing 1-4 of nitrogen(s), 1-2 of oxygen(s) and/or 1-2 of sulfur(s), with the proviso that these above groups are not OH, cyano, =N—$OR^{11A}$, or a group containing OH, cyano or =N—$OR^{11A}$.

In the compound of formula (B), 1-cyano-1-(2-methyl-4-methoxyphenyl)propan-2-one (Compound B-1), and 1-cyano-1-(2-chloro-4-methoxyphenyl)propane-2-one (Compound B-2) were described as Reference Examples, and it was shown that these compounds may be produced by a process described in scheme A and B.

Scheme A

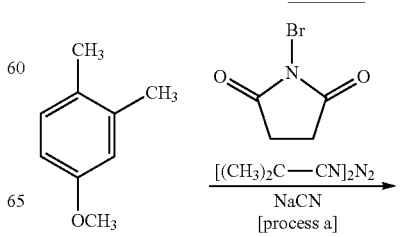

$\xrightarrow{[(CH_3)_2C\text{---}CN]_2N_2}$
NaCN
[process a]

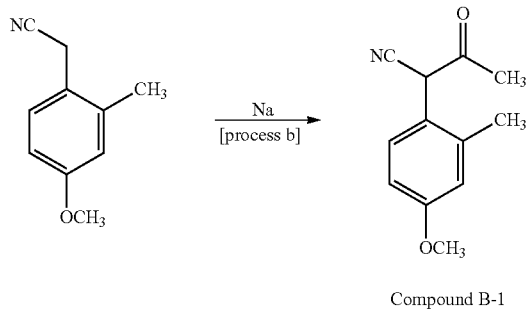

Compound B-1

Scheme B

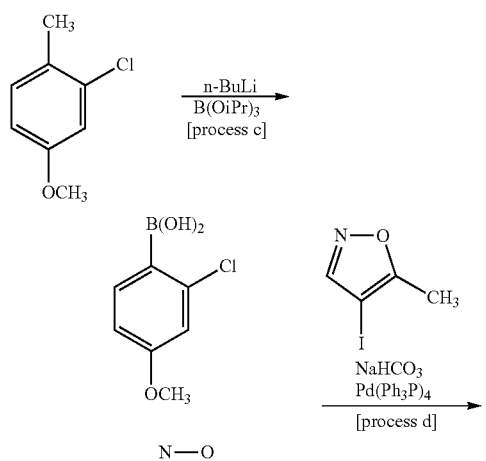

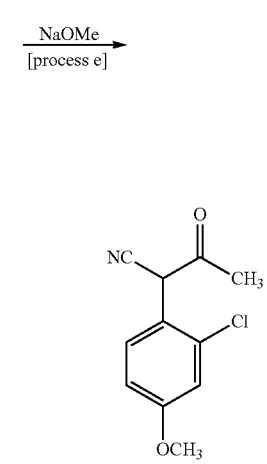

Compound B-2

[Process a] is carried out by the reaction of 1,2-dimethyl-4-methoxybenzene with N-bromosuccinimide and 2,2'-azobisisobutylonitrile, and then carried out by a reaction of the obtained compound and sodium cyanide.

[Process b] is carried out by the reaction of the compound prepared in [process A] and metallic sodium, in ethyl acetate.

[Process c] is carried out by the reaction of 3-chloro-4-bromoanisol and triisopropyl borate, in tetrahydrofuran, in the presence of n-butyl lithium.

[Process d] is carried out by the reaction of the compound prepared in [process c] and 4-iodo-5-methylisoxazole, in a mixture of dimethoxyethane/water, in the presence of sodium carbonate and tetrakis(triphenylphosphine)palladium.

[Process e] is carried out by the reaction of the compound prepared in [process d] and sodium methoxide, in methanol.

In WO 02/053565, as a concrete compound, 8-(3-pentylamino)-2-methyl-3-(2-chloro-4-methoxyphenyl)-6,7-dihydro-5H-cyclopenta[d]pyrazolo[1,5-a]pyrimidine hydrochloride was described. However, the thermal stability of this compound was poor. It separated and escape of hydrochloric acid occurred above a certain temperature. In addition, crystallinity of this compound was poor, and a yield of the crystal was very low.

As described above, it was difficult to provide stability to the hydrochloride compound possessing characteristics of inferior thermal stability and a low yield of crystal. Additionally, a problem may be caused if a heating process is necessary in the production of drug products, therefore, the hydrochloride compound was undesirable as a pharmaceutical drug substance.

Further, in the process for the preparation of the intermediate of formula (B) described above, the reaction of [process b] using metallic sodium in scheme A required specialized equipment under strong alkali condition, so it was not adequate for industrial production. Additionally, a total yield of the compound B-1 in the two processes of [process a] and [process b] was low, in particular 59%.

In the reaction of scheme B, 4-iodo-5-methylisoxazole used in [process d] was not adequate for industrial production. The reason is that procurement of methyl isoxazole, which is the starting material for 4-iodo-5-methylisoxazole, was difficult. Additionally, three processes were needed to produce the compound B-2, and a total yield was low, in particular 27%.

As described above, the preparation process described in WO 02/053565 has some problems, for example, a lot of processes, a low yield of the objective compound and inferior industrial productivity.

The present inventors have made extensive studies to solve the above problems, and as a result, have found that the object is achieved by a novel compound of 8-(3-pentylamino)-2-methyl-3-(2-chloro-4-methoxyphenyl)-6,7-dihydro-5H-cyclopenta[d]pyrazolo[1,5-a]pyrimidine methanesulfonate and a novel crystal thereof.

Additionally, the present inventors have discovered a process for the preparation of a compound of formula (I)

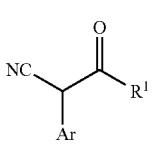

(I)

wherein all symbols are as hereinafter defined, which could be prepared by reacting the compound of formula (II)

Ar—X (II)

wherein all symbols are as hereinafter defined,
and a compound of formula (III)

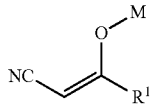

(III)

wherein all symbols are as hereinafter defined,
in the presence of a homogeneous catalyst.

The compound of formula (I) was an intermediate of 8-(3-pentylamino)-2-methyl-3-(2-chloro-4-methoxyphenyl)-6,7-dihydro-5H-cyclopenta[d]pyrazolo[1,5-a]pyrimidine methanesulfonate which is useful for pharmaceuticals, and the process was one step and efficient. Also the objective compound was possible to obtain in high yield.

DISCLOSURE OF INVENTION

Figure 1:
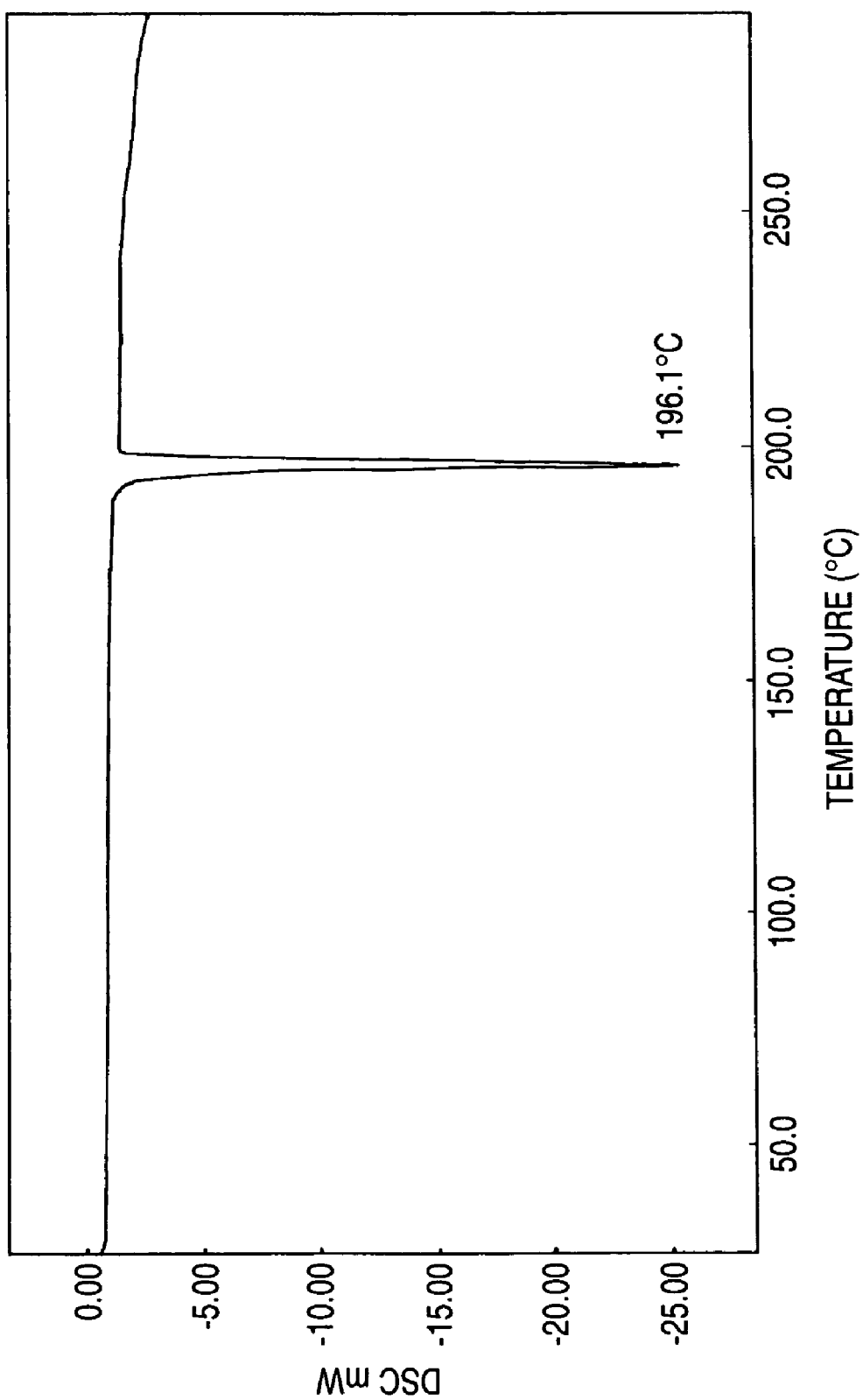
FIG. 1 shows a differential scanning calorimetry chart of 8-(3-pentylamino)-2-methyl-3-(2-chloro-4-methoxyphenyl)-6,7-dihydro-5H-cyclopenta[d]pyrazolo[1,5-a]pyrimidine methanesulfonate.

The present invention relates to:
1. 8-(3-pentylamino)-2-methyl-3-(2-chloro-4-methoxyphenyl)-6,7-dihydro-5H-cyclopenta[d]pyrazolo[1,5-a]pyrimidine methanesulfonate.
2. A crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate.
3. A crystal according to the above-mentioned 2, which has X-ray powder diffraction spectrum shown in FIG. 3.
4. A crystal according to the above-mentioned 2, which has diffraction angle 2θ at 8.96, 12.70, 13.69, 14.98, 15.74, 16.38, 17.63, 18.98, 19.71, 20.49, 21.37, 22.26, 22.88, 23.76, 24.70, 25.79 and 26.57 on X-ray powder diffraction spectrum.
5. A crystal according to the above-mentioned 2, which has infrared resonance spectrum shown in FIG. 4.
6. A crystal according to the above-mentioned 2, which has absorption of infrared resonance spectrum at 1652, 1595, 1549, 1220, 1168, 1141, 1115, 1034, 790, 766, 548, 533 and 522 $cm^{-1}$.
7. A process for the preparation of 8-(3-pentylamino)-2-methyl-3-(2-chloro-4-methoxyphenyl)-6,7-dihydro-5H-cyclopenta[d]pyrazolo[1,5-a]pyrimidine methanesulfonate, which comprises reacting 8-(3-pentylamino)-2-methyl-3-(2-chloro-4-methoxyphenyl)-6,7-dihydro-5H-cyclopenta[d]pyrazolo[1,5-a]pyrimidine with methanesulfonic acid.
8. A pharmaceutical composition comprising the compound described in the above-mentioned 1 as an active ingredient.
9. A pharmaceutical composition comprising 1% or more of a crystal, as an active ingredient, described in any one of the above-mentioned 2-6.
10. A pharmaceutical composition according to the above-mentioned 8, which is a CRF antagonist.
11. A pharmaceutical composition according to the above-mentioned 8, which is a prevention and/or treatment agent of a CRF mediated disease.
12. A pharmaceutical composition according to the above-mentioned 11, wherein the CRF mediated disease is a neuropsychiatric disorder or a digestive system disease.
13. A pharmaceutical composition according to the above-mentioned 12, wherein the neuropsychiatric disorder is a mood disorder, an anxiety disorder, a stress related disorder, an eating disorder, a symptom by psychotomimetic drug use and dependence, an organic mental disorder, schizophrenia or an attention-deficit hyperactivity disorder.
14. A pharmaceutical composition according to the above-mentioned 12, wherein the digestive system disease is an irritable bowel syndrome or a stress-induced gastrointestinal disturbance.
15. A pharmaceutical composition according to the above-mentioned 13, wherein the mood disorder is depression, single episode depression, recurrent depression, postpartum depression, child abuse induced depression, bipolar affective disorder or premenstrual dysphonic disorder.
16. A medicine which comprises 8-(3-pentylamino)-2-methyl-3-(2-chloro-4-methoxyphenyl)-6,7-dihydro-5H-cyclopenta[d]pyrazolo[1,5-a]pyrimidine methanesulfonate and one or more medicaments selected from tricyclic antidepressants, tetracyclic antidepressants, monoamine oxidase inhibitors, serotonin-noradrenaline reuptake inhibitors, selective serotonin reuptake inhibitors, serotonin reuptake inhibitors, psychoanaleptics, antianxiety agents, antipsychotic agents, mitochondrial benzodiazepine receptor ligands, NK1 antagonists, gastrointestinal promotility agents, 5-$HT_3$ antagonists, 5-$HT_4$ agonists, anticholinergic agents, antidiarrheal drugs, lapactic and autonomic nerve modulators.
17. A CRF antagonist comprising 8-(3-pentylamino)-2-methyl-3-(2-chloro-4-methoxyphenyl)-6,7-dihydro-5H-cyclopenta[d]pyrazolo[1,5-a]pyrimidine methanesulfonate as an active ingredient.
18. An injection comprising 8-(3-pentylamino)-2-methyl-3-(2-chloro-4-methoxyphenyl)-6,7-dihydro-5H-cyclopenta[d]pyrazolo[1,5-a]pyrimidine methanesulfonate.
19. The injection according to the above-mentioned 18, which comprises a solubilizing agent and/or a pH adjuster.
20. A method for antagonizing CRF, which comprises administering an effective amount of 8-(3-pentylamino)-2-methyl-3-(2-chloro-4-methoxyphenyl)-6,7-dihydro-5H-cyclopenta[d]pyrazolo[1,5-a]pyrimidine methanesulfonate to mammals.
21. Use of 8-(3-pentylamino)-2-methyl-3-(2-chloro-4-methoxyphenyl)-6,7-dihydro-5H-cyclopenta[d]pyrazolo[1,5-a]pyrimidine methanesulfonate for preparing a CRF antagonist.

22. A process for the preparation of a compound of formula (I)

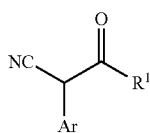
(I)

wherein all symbols are as hereinafter defined;
which comprises reacting a compound of formula (II)

Ar—X    (II)

wherein Ar is benzene, naphthalene, pyridine, 1,3-dioxaindan or benzothiadiazole that rings may be substituted by substituents, X is halogen atom;
with a compound of formula (III)

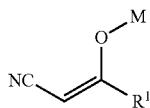
(III)

wherein $R^1$ is (i) C1-8 alkyl, (ii) C2-8 alkenyl, (iii) C2-8 alkynyl, (iv) trifluoromethyl, (v) C3-10 mono- or bi-carbocyclic ring, (vi) 3- to 10-membered mono- or bi-heterocyclic ring containing 1-4 of nitrogen(s), 1-2 of oxygen(s) and/or 1-2 of sulfur(s), (vii) C1-4 alkyl substituted by 1-2 of selected from trifluoromethyl, $NR^3R^4$ in which $R^3$ and $R^4$ each, independently, is (i) hydrogen, (ii) C1-4 alkyl, (iii) C3-10 mono- or bi-carbocyclic ring, (iv) 3- to 10-membered mono- or bi-heterocyclic ring containing 1-4 of nitrogen(s), 1-2 of oxygen(s) and/or 1-2 of sulfur(s) or (v) C1-4 alkyl substituted by C3-10 mono- or bi-carbocyclic ring or 3- to 10-membered mono- or bi-heterocyclic ring containing 1-4 of nitrogen(s), 1-2 of oxygen(s) and/or 1-2 of sulfur(s); $OR^5$ in which $R^5$ is (i) hydrogen, (ii) C1-4 alkyl, (iii) C5-6 carbocyclic ring, (iv) 5- or 6-membered heterocyclic ring containing 1-2 of nitrogen(s), 1 of oxygen and/or 1 of sulfur or (v) C1-4 alkyl substituted by C5-6 carbocyclic ring or 5- or 6-membered heterocyclic ring containing 1-2 of nitrogen(s), 1 of oxygen and/or 1 of sulfur; $S(O)nR^6$ in which n is 0, 1 or 2, $R^6$ is (i) C1-4 alkyl, (ii) C5-6 carbocyclic ring, (iii) 5- or 6-membered heterocyclic ring containing 1-2 of nitrogen(s), 1 of oxygen and/or 1 of sulfur or (iv) C1-4 alkyl substituted by C5-6 carbocyclic ring or 5- or 6-membered heterocyclic ring containing 1-2 of nitrogen(s), 1 of oxygen and/or 1 of sulfur; $COR^5$, $COOR^5$, $CONR^3R^4$, C3-10 mono- or bi-carbocyclic ring and 3- to 10-membered mono- or bi-heterocyclic ring containing 1-4 of nitrogen(s), 1-2 of oxygen(s) and/or 1-2 of sulfur(s); M is a metal atom,
in the presence of a homogeneous catalyst.

23. The process for the preparation according to the above-mentioned 22, wherein the homogeneous catalysts is palladium series.

8-(3-Pentylamino)-2-methyl-3-(2-chloro-4-methoxyphenyl)-6,7-dihydro-5H-cyclopenta[d]pyrazolo[1,5-a]pyrimidine methanesulfonate (hereinafter called the compound (1)) of the present invention is a novel compound.

Even more surprising, compound (1) is a compound superior in thermal stability as shown by the DSC chart in FIG. 1 which has an absorption peak at 196.1° C.

Figure 2:
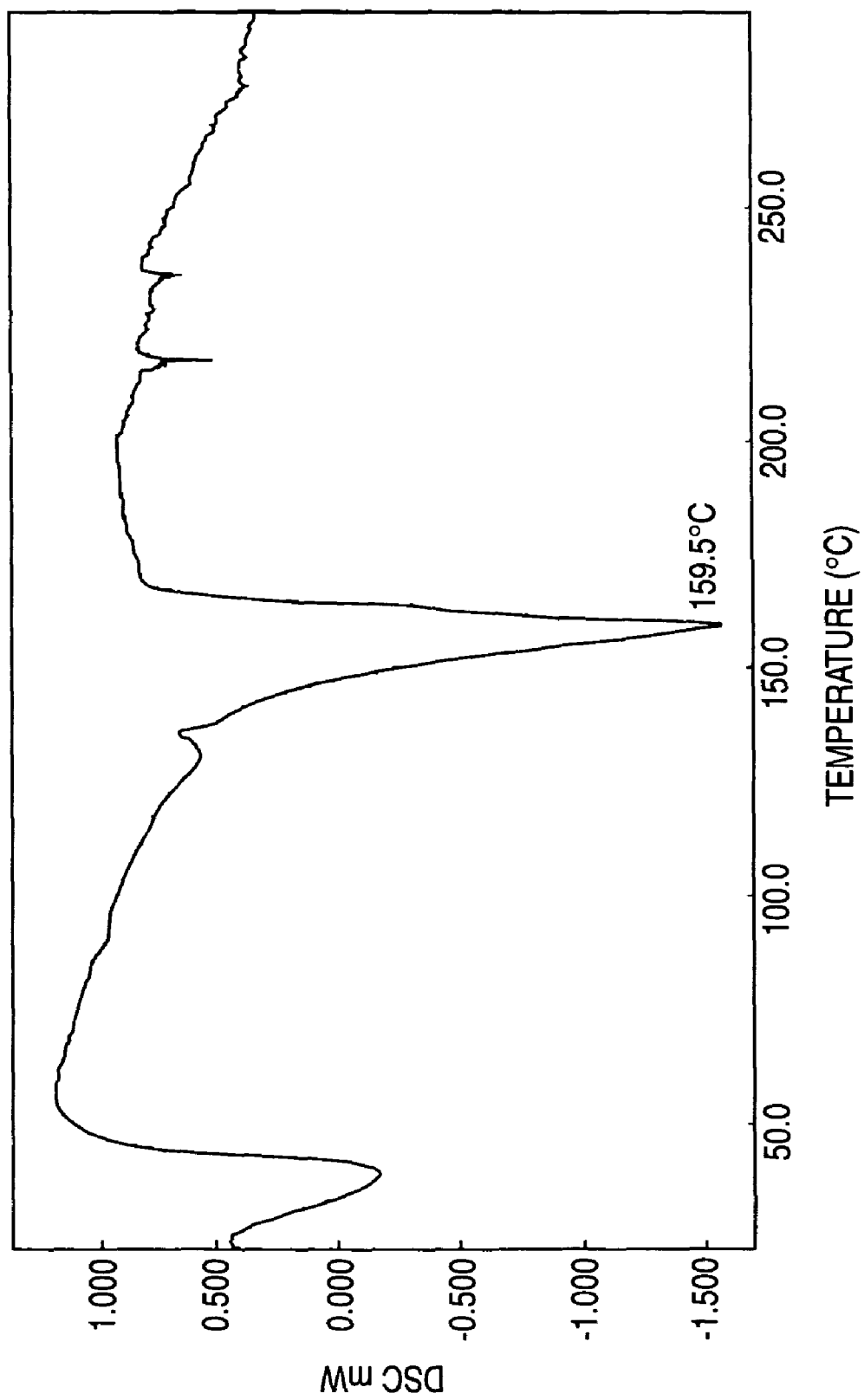
FIG. 2 shows a differential scanning calorimetry chart of 8-(3-pentylamino)-2-methyl-3-(2-chloro-4-methoxyphenyl)-6,7-dihydro-5H-cyclopenta[d]pyrazolo[1,5-a]pyrimidine hydrochloride.

On the other hand, DSC chart of 8-(3-pentylamino)-2-methyl-3-(2-chloro-4-methoxyphenyl)-6,7-dihydro-5H-cyclopenta[d]pyrazolo[1,5-a]pyrimidine hydrochloride described in WO 02/053565 is shown in FIG. 2. A stable DSC curve as in FIG. 1 was not shown in FIG. 2, and the curve once changed significantly at near 40° C., and then changed gradually after over 50° C.

From these results, it was determined that the hydrochloride compound is an unstable compound to heat, and the methanesulfonate compound of the present invention is a compound having superior thermal stability. It was very surprising that the difference of the salt influenced heat stability like this greatly, and it was not easily expected.

Additionally, the present compound was remarkably superior also in solubility and disposition. And, a yield of crystal of the present compound was very high as it was obtained at a high yield of 98% in Example described below and the present compound was adequate for industrial production as a pharmaceutical drug substance.

The present compound (1) which has such superior characteristics can be supplied stably, is adequate for industrial production and is superior in the formation of a drug product.

Toxicity

The toxicity of compound (1) of the present invention is very low and therefore the compound may be considered safe for pharmaceutical use.

INDUSTRIAL APPLICABILITY

Application for Pharmaceuticals

Compound (1) is useful, to bind a CRF receptor and show CRF receptor antagonistic activity, for the prevention and/or treatment of diseases associated with CRF, for example, neuropsychiatric disorders, digestive system diseases, respiratory diseases, endocrine diseases, metabolic diseases, circulatory system diseases, skin diseases, urogenital diseases, eye diseases, musculoskeletal system diseases.

Concretely, as neuropsychiatric disorders, for example, mood disorders, such as depression, single episode depression, recurrent depression, postpartum depression, child abuse induced depression, bipolar disorders, premenstrual dysphoric disorder; anxiety disorders, such as anxiety related disorders, panic disorder, obsessive compulsive disorder, phobic disorders, e.g., acrophobia, claustrophobia, agoraphobia, social phobia; stress related disorders, such as posttraumatic stress disorder (PTSD), stress-induced immune depression, stress-induced headache, stress-induced fever, stress-induced pain, surgery induced stress, surgery induced gastrointestinal disorder, irritable bowel syndrome; eating disorders, such as anorexia nervosa, binge eating disorder, nervous emesis; symptoms by psychotomimetic drug use and dependence, such as abstinence symptom, alcoholism, drug intoxication, drug dependence; organic mental disorders, such as dementia of the Alzheimer type, multiple infarct dementia; schizophrenia, attention-deficit hyperactivity disorder, neurodegenerative disease, e.g., Alzheimer's disease, Parkinson's disease, Huntington's disease, amyotrophic lateral sclerosis; pain, convulsive disorders, such as convulsions, muscle spasm; seizure disorder, such as epilepsy, attack, migraine; or sleep disorder, such as nonorganic sleep disorder, fibromyalgia induced sleep disorder are given.

As digestive system diseases, for example, peptic ulcer, inflammatory bowel disease, e.g., ulcerative colitis, Crohn's disease; irritable bowel syndrome, stress induced gastrointestinal disturbance, diarrhea and constipation are given.

As respiratory diseases, for example, asthma, bronchial infection, chronic obstructive pulmonary disease and allergic rhinitis are given.

As endocrine diseases, for example, thyroidal dysfunction syndrome, Cushing's disease and syndrome of inappropriate antidiuretic hormone secretion are given.

As metabolic diseases, for example, obesity and hypoglycemia are given.

As circulatory system diseases, for example, hypertension, ischemic heart disease, tachycardia, congestive heart failure and cerebrovascular disease are given.

As skin diseases, atopic dermatitis, for example, allergic contact dermatitis and psoriasis are given.

As urogenital diseases, for example, urinary disturbance, pollakiuria and incontinence are given.

As eye diseases, for example, uveitides is given.

As musculoskeletal system diseases, for example, chronic rheumatoid arthritis, osteoarthritis and osteoporosis are given.

A combination agent obtained by combining the compound (1) with other medicaments may be administered to accomplish the following purposes:
1) to supplement and/or enhance the preventive and/or therapeutic effect of the present compound;
2) to improve the kinetics and/or absorption and reduce the dose of the present compound; and/or
3) to eliminate the side effects of the present compound.

A combination of the compound (1) of the present invention and other medicaments may be administered in the form of formulations having these components incorporated in one preparation, or may be administered in separate preparations. In the case where these medicaments are administered in separate preparations, they may be administered simultaneously or at different times. In the latter case, compound (1) may be administered before the other medicaments. Alternatively, the other medicaments may be administered before compound (1). The method for the administration of these medicaments are the same or different.

The diseases on which the preventive and/or therapeutic effect of the above mentioned combination preparations works are not specifically limited but may be those for which the preventive and/or therapeutic effect of the compound (1) is supplemented and/or enhanced.

Examples of other medicaments for supplementing and/or enhancing the preventive and/or therapeutic effect of compound (1) of the present invention on mood disorders include an antidepressant, such as a tricyclic antidepressant, a tetracyclic antidepressant, a monoamine oxidase (MAO) inhibitor, a serotonin-noradrenaline reuptake inhibitor (SSRI), a serotonin reuptake inhibitor; a psychoanaleptic, an antianxiety agent, an antipsychotic agent, a mitochondrial benzodiazepine receptor (MBR) ligand, an NK1 antagonist, and the like.

Examples of other medicaments for supplementing and/or enhancing the preventive and/or therapeutic effect of compound (1) of the present invention on anxiety disorders include an antianxiety agent, such as a benzodiazepine anxiolytic, a thienodiazepine anxiolytic, a non-benzodiazepine anxiolytic, a MBR ligand, and the like.

Examples of other medicaments for supplementing and/or enhancing the preventive and/or therapeutic effect of the compound (1) on irritable bowel syndrome include a gastrointestinal promotility regulator, a 5-$HT_3$ antagonist, a 5-$HT_4$ agonist, an anticholinergic agent, an antidiarrheal drug, a lapactic, an autonomic nerve modulator, an antidepressant, an antianxiety agent, and the like.

As an antidepressant, for example, a tricyclic antidepressant, such as amitriptyline hydrochloride, imipramine hydrochloride, clomipramine hydrochloride, dosulepin hydrochloride, nortriptyline hydrochloride, lofepramine hydrochloride, trimipramine maleate, and amoxapine; a tetracyclic antidepressant, such as maprotiline hydrochloride, mianserin hydrochloride, and setiptiline maleate; a MAO inhibitor, such as safrazine hydrochloride; a SNRI, such as milnacipran hydrochloride, and venlafaxine hydrochloride; a SSRI, such as fluvoxamine maleate, paroxetine hydrochloride, fluoxetine hydrochloride, and citalopram hydrochloride; and a serotonin reuptake inhibitor, such as trazodone hydrochloride, are given.

As an antianxiety agent, for example, a benzodiazepine anxiolytic, such as alprazolam, oxazepam, oxazolam, cloxazolam, clorazepate dipotassium, chlordiazepoxide, diazepam, tofisopam, triazolam, prazepam, fludiazepam, flutazolam, flutoprazepam, bromazepam, mexazolam, medazepam, ethyl loflazepate, a lorazepam; a thienodiazepine anxiolytic, such as etizolam, and clotiazepam; a non-benzodiazepine anxiolytic, such as tandospirone citrate and hydroxylzine hydrochloride, are given.

As a psychoanaleptic, for example, methylphenidate hydrochloride and pemoline are given.

As an antipsychotic agent, for example, sulpiride, trazodone hydrochloride, a serotonin-dopamine antagonist such as risperidone, perospirone hydrochloride hydrate, quetiapine fumarate and olanzapine are given.

As a gastrointestinal regulator, for example, trimebutine maleate and polycarbophil calcium are given.

As a 5-$HT_3$ antagonist, for example, alosetron is given.

As a 5-$HT_4$ agonist, for example, tegaserod, cisapride and mosapride citrate are given.

The weight ratio of compound (1) and the other medicaments is not specifically limited.

Any combination of two or more other medicaments may be administered.

Furthermore, the other medicaments for supplementing and/or enhancing the preventive and/or therapeutic effect of the compound (1) include not only those found so far but also those which will be found on the basis of the above mentioned mechanism.

As the form of the preparation, for example, solid preparations for internal use and liquid preparations for internal use for oral administration, injections, external preparations and suppositories for parenteral administration are given.

Examples of the solid preparations for internal use for oral administration include tablets, pills, capsules, powders, granules and the like. The capsules include hard capsules and soft capsules.

Such a solid preparation for internal use is prepared by a formulation method commonly employed by using an active substance without modification, or a mixture of an active substance with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer (e.g., antioxidant such as sulfite salt, sodium pyrosulfite, ascorbic acid), a solubilizing agent (glutamic acid, aspartic acid, polysorbate series such as Polysorbate 20, Polysorbate 60, Polysorbate 65, Polysorbate 80; macrogol series such as Macrogol 200, Macrogol 400, Macrogol 1000, Macrogol 1500, Macrogol 4000, Macrogol 6000, Macrogol 20000; ethanol, glycerin, carboxymethyl cellulose, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are included in the scope thereof.

The liquid preparations for internal use for oral administration include pharmaceutically acceptable aqueous solutions, suspensions, emulsions, syrups, elixirs and the like. Such a liquid preparation is prepared by dissolving, suspending or emulsifying an active substance in a diluent commonly employed (purified water, ethanol or a mixture thereof, etc.). Such liquid forms may also further comprise some additives such as humectants, suspending agents, emulsifying agents, sweetening agents, flavoring agents, aroma, preservatives, buffers and the like.

The injections for parenteral administration include solutions, suspensions, emulsions and solid injections to be dissolved or suspended before use. Such an injection is used by dissolving, suspending or emulsifying an active substance in a solvent. The solvent includes, for example, distilled water for injection, physiological saline, vegetable oils, alcohols such as propylene glycol, polyethylene glycol and ethanol, and mixtures thereof. The injection may further contain a stabilizer (e.g., antioxidant such as sulfite salt, sodium pyrosulfite, ascorbic acid), a solubilizing agent (e.g., glutamic acid, aspartic acid, polysorbate series such as Polysorbate 20, Polysorbate 60, Polysorbate 65, Polysorbate 80; macrogol series such as Macrogol 200, Macrogol 400, Macrogol 1000, Macrogol 1500, Macrogol 4000, Macrogol 6000, Macrogol 20000; ethanol, glycerin, carboxymethyl cellulose etc.), pH modulator (e.g., hydrochloric acid, citric acid, sodium citrate, acetic acid, tartaric acid, succinic acid, arginine, monoethanolamine, diethanolamine, triethanolamine, meglumine, sodium hydroxide, potassium hydroxide, sodium bicarbonate, sodium carbonate), suspending agents, emulsifying agents, soothing agent (e.g., chlorobutanol, creatinine, inositol), buffering agent (e.g., phosphoric acid, trisodium phosphate, sodium hydrogenphosphate, dipotassium phosphate, potassium dihydrogen phosphate, sodium dihydrogen phosphate), preservative (e.g., methyl parahydroxybenzoate, ethyl parahydroxybenzoate, propyl parahydroxybenzoate, butyl parahydroxybenzoate) and the like. Such an injection may be produced by sterilizing at the final step or employing an aseptic process. Alternatively, it is also possible that an aseptic solid product such as a freeze-dried product is produced and sterilized or dissolved in aseptic distilled water for injection or another solvent, such as physiological saline, 5% glucose solution before use.

The external preparations for parenteral administration include ointments, gels, creams, fomentations, patches, liniments, atomized agents, inhalations, sprays, eye drops and nasal drops and the like. Such a preparation contains an active substance and is prepared by a well known method or a commonly employed formulation.

Other compositions for parenteral administration include suppositories and pessaries for vaginal administration which contain one or more active substances, and are prepared in accordance with common formulations.

Compound (1) of the present invention is a novel crystal characterized by the following data.

In other words, the crystal is characterized by X-ray powder diffraction spectrum, which was obtained by irradiation of Cu-Kα, shown in FIG. 3; and data of a diffraction angle 2θ and relative intensity shown in the following Table 1.

TABLE 1

| angle of diffraction (2θ) | relative intensity |
| --- | --- |
| 8.96 | 44 |
| 12.70 | 13 |

TABLE 1-continued

| angle of diffraction (2θ) | relative intensity |
| --- | --- |
| 13.69 | 21 |
| 14.98 | 10 |
| 15.74 | 20 |
| 16.38 | 13 |
| 17.63 | 44 |
| 18.98 | 19 |
| 19.71 | 45 |
| 20.49 | 32 |
| 21.37 | 99 |
| 22.26 | 32 |
| 22.88 | 31 |
| 23.76 | 40 |
| 24.70 | 27 |
| 25.79 | 100 |
| 26.57 | 22 |

Figure 4:
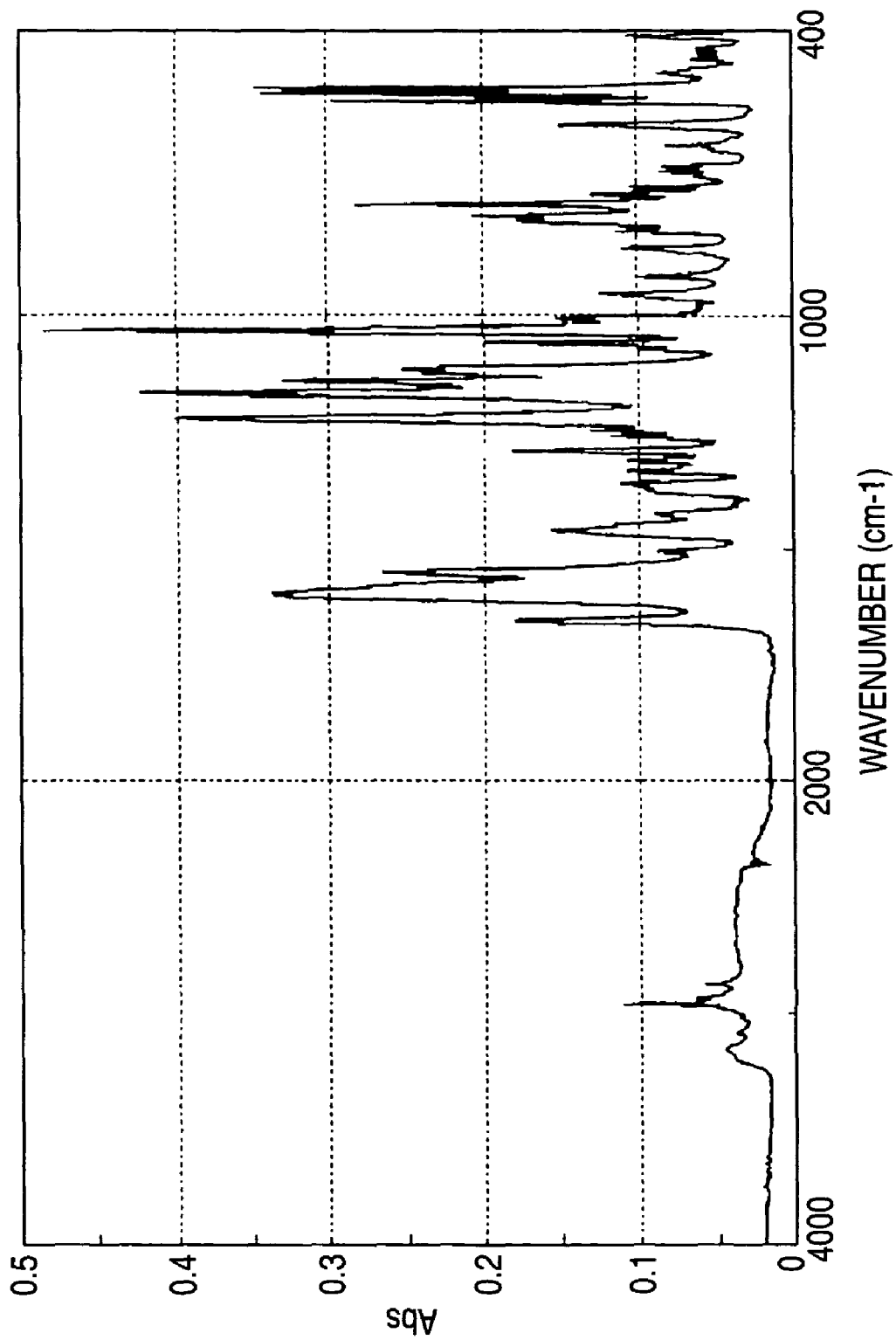
FIG. 4 shows a chart of infrared resonance (IR) spectrum of a crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate.

In addition, the crystal is characterized by absorption of infrared resonance (IR) spectrum at 1652, 1595, 1549, 1220, 1168, 1141, 1115, 1034, 790, 766, 548, 533, 522 cm$^{-1}$, and an IR spectrum measured by ATR method is shown in FIG. 4.

Furthermore, the crystal is also characterized by an absorption peak at 196.1° C. in the DSC chart shown in FIG. 1.

The crystal of compound (1) is characterized by physicochemical properties described in the present specification, but each analysis data should not be interpreted strictly, because it changes somewhat on the character of the data.

For example, in the recognition of the identity of the crystal on the character of X-ray powder diffraction spectrum, the diffraction angle (2θ) and overall patterns are important, and the relative intensity can change somewhat depending on the growth direction of crystal, particle size and conditions of measurement. And, in IR spectrum, the overall pattern is important for the recognition of the identity of the crystal, and it can change somewhat depending on the measurement conditions. In data of DSC, the overall pattern is important for the recognition of crystal identity and it can change somewhat depending on the measurement condition.

Therefore, those crystals which have analogous data and patterns in X-ray diffraction spectrum, IR spectrum and DSC of the crystal of compound (1), are included in the crystal of compound (1) of the present invention.

Figure 3:
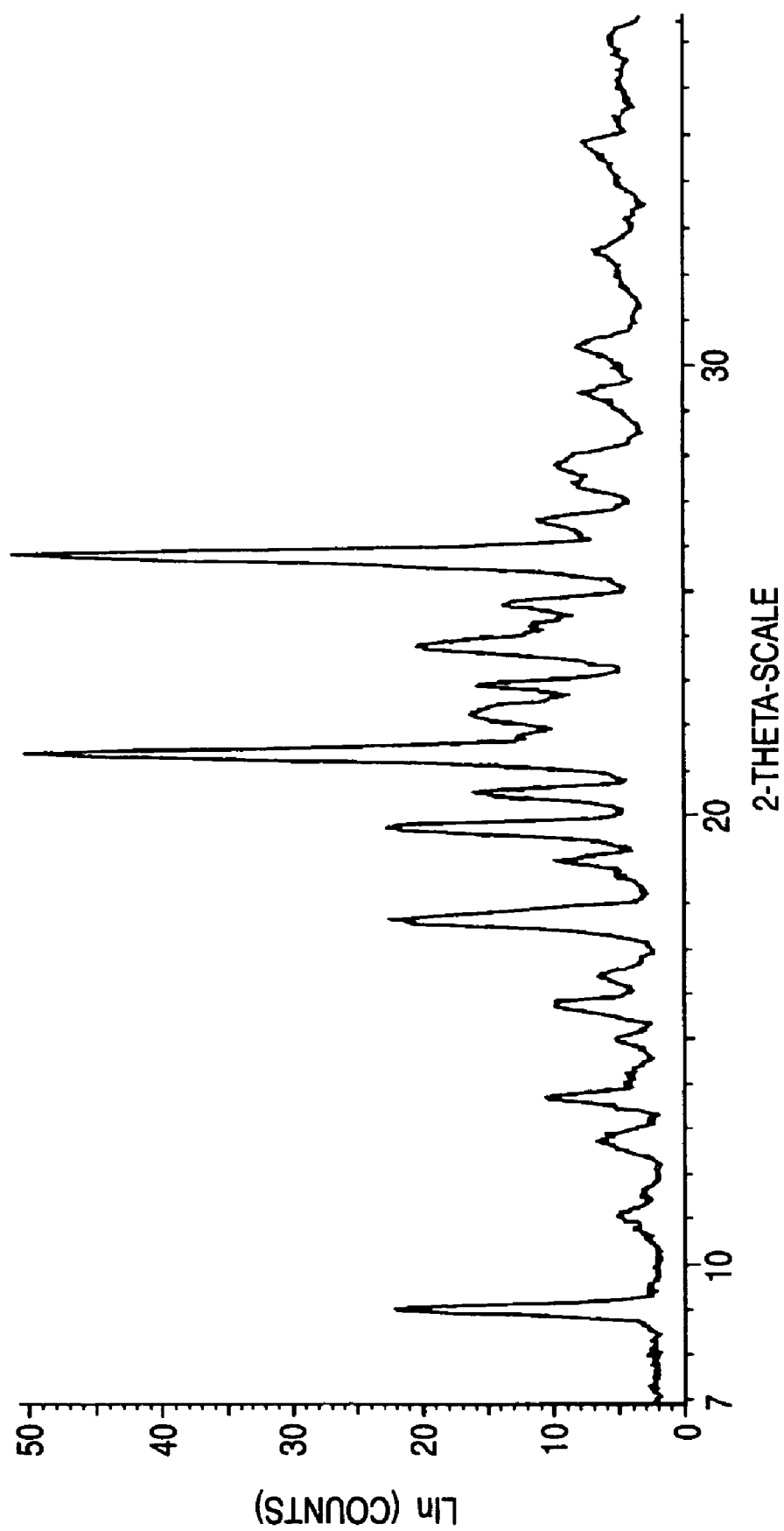
FIG. 3 shows a chart of X-ray powder diffraction spectrum of a crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate.

As the crystal of compound (1) of the present invention, the crystal type having X-ray powder diffraction spectrum shown in FIG. 3 and/or IR spectrum shown in FIG. 4 is preferred, but it may be a mixture compound with different crystal type that will be found in the future, and may be a mixture compound with non-crystalline material of compound (1).

The crystal of compound (1) of the present invention is steady for humidity and light, besides heat.

The compound of formula (I) is important as an intermediate in the manufacturing process of 8-(3-pentylamino)-2-methyl-3-(2-chloro-4-methoxyphenyl)-6,7-dihydro-5H-cyclopenta[d]pyrazolo[1,5-a]pyrimidine methanesulfonate.

The method for manufacturing the compound of formula (I) of the present invention is a process in which the objective compound can be obtained efficiently in high yield and, in which the problem that the prior art possesses is solved. The method of manufacture of the present invention is shown in the following scheme 1.

Scheme 1

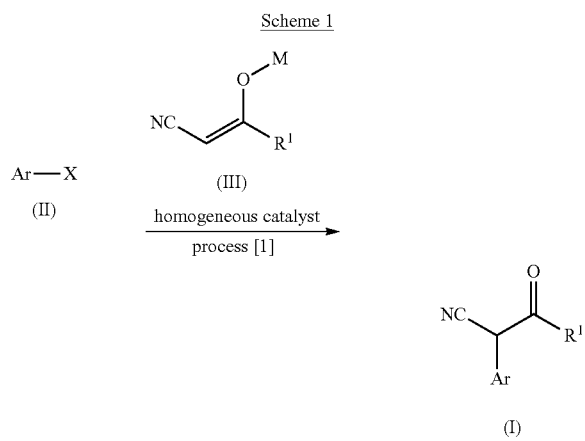

In Scheme 1, all symbols are as hereinbefore defined.

The compound of formula (I) can be manufactured by the method of the present invention from the compound of formula (II) by one process.

Process [1] is carried out in an organic solvent, for example, 1,2-dimethoxyethane, diglyme, toluene, xylene, dimethylformamide, cyclopentyl methyl ether, tetrahydrofuran, dioxane; in the presence of a base, for example, sodium t-butoxide, potassium t-butoxide, lithium t-butoxide, sodium hydride, sodium carbonate, potassium carbonate, lithium carbonate, potassium phosphate, sodium phosphate; in the presence or absence of iodide, using a homogeneous catalyst at 70 to 120° C.

The method of manufacture of the present invention is an excellent method in terms of industrial productivity, because each reagent can be easily procured, the reaction is one process and the objective compound can be obtained in high yield.

Preferable homogeneous catalysts in the present invention are in the palladium series of homogeneous catalysts. For example, tetrakis(triphenylphosphine)palladium, palladium acetate, tris(dibenzylidenacetone)dipalladium and palladium chloride are given. The quantity consumed is a catalyst quantity, preferable quantity is 0.1 to 20 mol % for the starting material, more preferable quantity is 0.25 to 10 mol %, and especially 0.25 to 5 mol % is preferred.

In addition, homogeneous catalysts in the present invention are only homogeneous catalyst or a combination of homogeneous catalyst and a ligand. As the ligand, triphenylphosphine, 2,2'-bis(diphenylphosphino)-1,1'-binaphthyl, 9,9'-dimethyl-4,5-bis(diphenylphosphino)xanthene, 1,1'-bis(diphenylphosphino)ferrocene, 1,2-bis(diphenylphosphino)ethane, 1,3-bisu(diphenylphosphino)propane, 1,4-bis(diphenylphosphino)butane, tri-2-m-triphosphine, tri-p-tolylphosphine, tri-o-tolylphosphine, tris(2-methoxyphenyl)phosphine, tris(3-methoxyphenyl)phosphine, tris(4-methoxyphenyl)phosphine, 1,2-bis(diphenylphosphino)benzene, trimethylsilylphosphine, tris(4-fluorophenyl)phosphine, tris(pentafluorophenyl)phosphine, cyclohexyldiphenylphosphine, dicyclohexylphenylphosphine, tris(3-sulfophenyl)phosphine trihydrochloride, bis(2-diphenylphosphinophenyl)ether, cis-1,2-bis(diphenylphosphino)ethylene, diphenyl pentafluorophenyl phosphine, 2-(di-t-butylphosphino)biphenyl, 2-(dicyclohexylphosphino)biphenyl, 2-dicyclohexylphosphino-2'-(N,N-dimethylamino)biphenyl are given. Preferable ligands are 1,2-bis(diphenylphosphino)ethane, tri-2-m-tolylphosphine, tri-p-tolylphosphine and 2,2'-bis(diphenylphosphino)-1,1'-binaphthyl.

In the present invention, as a homogeneous catalyst or a combination of homogeneous catalyst and a ligand, tetrakis(triphenylphosphine)palladium alone, palladium acetate and 1,2-bis(diphenylphosphino)ethane, palladium acetate and tri-2-m-tolylphosphine, palladium acetate and tri-p-tolylphosphine, palladium acetate and 2,2'-bis(diphenylphosphino)-1,1'-binaphthyl, tris(dibenzylidenacetone)dipalladium and 1,2-bis(diphenylphosphino)ethane, tris(dibenzylidenacetone)dipalladium and tri-2-m-tolylphosphine, tris(dibenzylidenacetone)dipalladium and tri-p-tolylphosphine, tris(dibenzylidenacetone)dipalladium and 2,2'-bis(diphenylphosphino)-1,1'-binaphthyl are preferable.

In the present invention, iodide means a compound that can generate an iodide ion in a reaction solution. For example, sodium iodide, potassium iodide, lithium iodide, rubidium iodide, cesium iodide, magnesium iodide, manganese iodide, iron iodide, cobalt iodide, nickel iodide, copper iodide, zinc iodide, silver iodide, quaternary ammonium iodide (e.g., tetra-n-butylammonium iodide), iodine are given as examples. The quantity consumed of iodide in the reaction is 0.3 to 2.0 equivalent for the compound of formula (II). Preferably, it is 0.3 to 1.0 equivalent.

In the present invention, when the objective compound has hydroxyl, carboxyl, SH or amino as substituents, the reaction may be carried out using the compound having hydroxyl, carboxyl, SH or amino protected by preferable protecting group, and then a deprotection reaction may be chosen to suit protecting groups.

For example, methyl, ethyl, allyl, tert-butyl, trichloroethyl, benzyl (Bn), phenacyl, p-methoxybenzyl, trityl, 2-chlorotrityl or solid phase carrier to which the group was bound, may be used as protecting groups for carboxyl.

Methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) may be used as protecting groups for hydroxyl.

Benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) may be used as protecting groups for amino and amidino.

Benzyl, methoxybenzyl, methoxymethyl (MOM), 2-tetrahydropyranyl (THP), diphenylmethyl and acetyl (Ac) may be used as protecting groups for thiol.

As protecting groups for carboxyl, hydroxyl or amino, other groups which can be removed easily and selectively other than the above protecting groups, are also preferred. For example, the groups described in T. W. Greene, *Protective Groups in Organic Synthesis*, Wiley, New York, 1999, may be used.

In the present invention, "substituents" of "benzene, naphthalene, pyridine, 1,3-dioxaindan or benzothiadiazole which rings may be substituted by substituents" means (a) C1-8 alkyl, (b) C2-8 alkenyl, (c) C2-8 alkynyl, (d) halogen atom, (e) trifluoromethyl, (f) trifluoromethoxy, (g) cyano, (h) nitro, (i) $NR^3R^4$, (k) $OR^5$, (l) SH, (m) $S(O)_nR^6$, (n) $COR^5$, (o) $COOR^5$, (p) $CONR^3R^4$, (q) $NR^7COR^5$, (r) $NR^7COOR^5$, (s) $NR^3CONR^3R^4$, (t) C3-10 mono- or bi-carbocyclic ring, (u) 3- to 10-membered mono- or bi-heterocyclic ring containing 1-4 of nitrogen(s), 1-2 of oxygen(s) and/or 1-2 of sulfur(s), or (v) C1-4 alkyl substituted by 1-2 of substitutes selected from halogen atom, trifluoromethyl, trifluoromethoxy, cyano, nitro, $NR^3R^4$, $OR^5$, =N—$OR^5$, SH, $S(O)_nR^6$, $COR^5$, $COOR^5$, $CONR^3R^4$, C3-10 mono- or bi-carbocyclic ring, and 3- to 10-membered mono- or bi-heterocyclic ring containing 1-4 of nitrogen(s), 1-2 of oxygen(s) and/or 1-2 of sulfur(s).

$R^3$, $R^4$, $R^5$, $R^6$ and n are as hereinbefore defined.

$R^7$ is (i) hydrogen, (ii) C1-8 alkyl, (iii) C2-8 alkenyl, (iv) C2-8 alkynyl, (v) C3-10 mono- or bi-carbocyclic ring, (vi) 3- to 10-membered mono- or bi-heterocyclic ring containing 1-4 of nitrogen(s), 1-2 of oxygen(s) and/or 1-2 of sulfur(s) or (vii) C1-4 alkyl substituted by 1-2 of substitutes selected from halogen atom, trifluoromethyl, $OCF_3$, cyano, nitro, $NR^3R^4$, $OR^5$, =N—$OR^5$, SH, $S(O)_nR^6$, $COR^5$, $COOR^5$, $CONR^3R^4$, C3-10 mono- or bi-carbocyclic ring, and 3- to 10-membered mono- or bi-heterocyclic ring containing 1-4 of nitrogen(s), 1-2 of oxygen(s) and/or 1-2 of sulfur(s).

In the present invention, preferable substituents of "benzene, naphthalene, pyridine, 1,3-dioxaindan or benzothiadiazole which rings may be substituted by substituents" are C1-8 alkyl, halogen atom, trifluoromethyl, trifluoromethoxy, cyano, $NR^{3a}R^{4a}$ in which $R^{3a}$ and $R^{4a}$ each independently, is hydrogen or C1-4 alkyl; $OR^{5a}$ in which $R^{5a}$ is hydrogen or C1-4 alkyl; $S(O)_nR^{6a}$ in which $R^{6a}$ is C1-4 alkyl; CHO, $COOR^{5a}$, $CONR^{3a}R^{4a}$, C3-7 cycloalkyl, phenyl, naphthyl, furyl, thienyl, pyrrolyl, pyridyl, or C1-4 alkyl substituted by 1-2 of substituents selected from halogen atom, trifluoromethyl, trifluoromethoxy, cyano, $NR^{3a}R^{4a}$, $OR^{5a}$, CHO, $COOR^{5a}$, $CONR^{3a}R^{4a}$, C3-7 cycloalkyl, phenyl, naphthyl, furyl, thienyl, pyrrolyl and pyridyl.

In the present invention, preferable Ar is benzene, pyridine or benzothiadiazole that may be substituted by the above substituents.

In the present invention, a halogen atom represented by X is chloride, bromide, fluoride or iodide, and chloride and bromide are preferable.

In the present invention, a metal atom represented by M is sodium, potassium or lithium, and sodium is preferable.

In the present invention, preferably $R^1$ is (i) C1-8 alkyl, (ii) C2-8 alkenyl, (iii) C2-8 alkynyl, or (iv) C1-4 alkyl substituted by 1-2 substituents selected from trifluoromethyl, $NR^3R^4$, $OR^5$, $S(O)_nR^6$, $COR^5$, $COOR^5$, $CONR^3R^4$, C3-10 mono- or bi-carbocyclic ring, and 3- to 10-membered mono- or bi-heterocyclic ring containing 1-4 of nitrogen(s), 1-2 of oxygen(s) and/or 1-2 of sulfur(s).

Especially, preferable $R^1$ is —$CH_2$—$R^2$. And preferably $R^2$ is (i) C1-7 alkyl, (ii) C2-7 alkenyl, (iii) C2-7 alkynyl, or (iv) trifluoromethyl, $NR^{3a}R^{4a}$, $OR^{5a}$, $S(O)_nR^{6a}$, $COR^{5a}$, $COOR^{5a}$, $CONR^{3a}R^{4a}$, C3-10 mono- or bi-carbocyclic ring or 3- to 10-membered mono- or bi-heterocyclic ring containing 1-4 of nitrogen(s), 1-2 of oxygen(s) and/or 1-2 of sulfur(s), or methylene substituted by them. Especially preferable $R^2$ is (i) C1-7 alkyl, or (ii) trifluoromethyl, $OR^{5a}$, $S(O)_1R^{6a}$, C3-7 cycloalkyl, phenyl, furyl, thienyl, pyrrolyl or pyridyl, or methylene substituted by them, in which $R^{3a}$, $R^{4a}$, $R^{5a}$ and $R^{6a}$ are as hereinbefore defined.

In the present invention, C1-4 alkyl includes methyl, ethyl, propyl, butyl and isomeric groups thereof.

In the present invention, C1-8 alkyl includes methyl, ethyl, propyl, butyl, pentyl, hexyl, heptyl, octyl and isomeric groups thereof.

In the present invention, C2-8 alkenyl includes ethyl, propyl, butyl, pentyl, hexyl, heptyl, octyl having 1-3 of double bond(s) and isomeric groups thereof. For example, vinyl, propenyl, butenyl, pentenyl, hexenyl, hexadienyl, heptenyl, heptadienyl, octenyl, and octadienyl are given.

In the present invention, C2-8 alkynyl includes ethyl, propyl, butyl, pentyl, hexyl, heptyl, octyl having 1-3 of triple bond(s) and isomeric groups thereof. For example, ethynyl, propynyl, butyryl, pentynyl, hexynyl, hexadiynyl, heptynyl, heptadiynyl, octynyl, and octadiynyl are given.

In the present invention, halogen atom includes fluorine, chlorine, bromine and iodine.

In the present invention, C5-6 carbocyclic ring is C5-6 carbocyclic aryl or partially or fully saturated thereof. For example, cyclopentane, cyclohexane, cyclopentene, cyclohexene, cyclopentadiene, cyclohexadiene, and benzene are given.

In the present invention, C3-7 cycloalkyl is cyclopropane, cyclobutane, cyclopentane, cyclohexane or cycloheptane.

In the present invention, C3-10 mono- or bi-carbocyclic ring is C3-10 c mono- or bi-carbocyclic aryl or partially or fully saturated thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, perhydropentalene, indan, perhydroindene, tetrahydronaphthalene, perhydronaphthalene, and perhydroazulene are given.

In the present invention, 5- or 6-membered heterocyclic ring containing 1-2 of nitrogen(s), 1 of oxygen and/or 1 of sulfur is 5- or 6-membered heterocyclic aryl containing 1-2 of nitrogen(s), 1 of oxygen and/or 1 of sulfur or partially or fully saturated thereof. For example, pyrrole, imidazole, pyrazole, pyridine, pyrazine, pyrimidine, pyridazine, furan, pyran, thiophene, thiain (thiopyran), oxazole, isoxazole, thiazole, isothiazole, pyrroline, pyrrolidine, piperidine, imidazoline, imidazolidine, pyrazoline, pyrazolidine, piperazine, perhydropyrimidine, perhydropyridazine, dihydrofuran, tetrahydrofuran, tetrahydropyran, dihydrothiophene, tetrahydrothiophene, tetrahydrothiain, morpholine, and thiomorpholine are given.

In the present invention, 3- to 10-membered mono- or bi-heterocyclic ring containing 1-4 of nitrogen(s), 1-2 of oxygen(s) and/or 1-2 of sulfur(s) is a 3- to 10-membered mono- or bi-heterocyclic aryl containing 1-4 of nitrogen(s), 1-2 of oxygen(s) and/or 1-2 of sulfur(s) or partially or fully saturated thereof.

The 3- to 10-membered mono- or bi-heterocyclic aryl containing 1-4 of nitrogen(s), 1-2 of oxygen(s) and/or 1-2 of sulfur(s) is, for example, pyrrole, imidazole, pyrazole, triazole, tetrazole, pyridine, pyrazine, pyrimidine, pyridazine, azepine, diazepine, furan, pyran, oxepine, thiophene, thiain (thiopyran), thiepine, oxazole, isoxazole, oxadiazole, oxazine, oxadiazine, oxazepine, oxadiazepine, thiazole, isothiazole, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, phthalazine, naphthyridine, quinoxaline, quinazoline, cinnoline, benzoxazole, benzoxadiazole, benzothiazole, benzimidazole, benzofurazan, benzothiadiazole, or benzotriazole.

The partially or fully saturated 3- to 10-membered mono- or bi-heterocyclic aryl containing 1-4 of nitrogen(s), 1-2 of oxygen(s) and/or 1-2 of sulfur(s) is, for example, aziridine, azetine, azetidine, pyrroline, pyrrolidine, imidazoline, imidazolidine, pyrazoline, pyrazolidine, triazoline, triazolidine, tetrazoline, tetrazolidine, piperidine, piperazine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiain (dihyrdothiopyran), tetrahydrothiain (tetrahydrothiopyran), dihydrothiepine, tetrahydrothiepine, perhydrothiepine, oxazoline (dihydrooxazole), oxazolidine (tetrahydrooxazole), dihydroisoxazole, tetrahydroisoxazole, oxadiazoline (dihydrooxadiazole), oxadiazolidine (tetrahydrooxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dioxolane, dioxane, dioxazine, dioxaindan, chroman, or isochroman.

In the present invention, salts superior in thermal stability of 8-(3-pentylamino)-2-methyl-3-(2-chloro-4-methoxyphenyl)-6,7-dihydro-5H-cyclopenta[d]pyrazolo[1,5-a]pyrimidine other than methanesulfonate are tosylate, benzenesulfonate and camphorsulfonate (D, L, or DL).

Preparation of the Compound of the Present Invention:

The present compound (1) may be prepared by reacting 8-(3-pentylamino)-2-methyl-3-(2-chloro-4-methoxyphenyl)-6,7-dihydro-5H-cyclopenta[d]pyrazolo[1,5-a]pyrimidine and methanesulfonic acid.

In detail, 8-(3-pentylamino)-2-methyl-3-(2-chloro-4-methoxyphenyl)-6,7-dihydro-5H-cyclopenta[d]pyrazolo[1,5-a]pyrimidine is dissolved in an organic solvent (e.g., ethyl acetate, methanol, tetrahydrofuran, 1,2-dimethoxyethane, isopropyl alcohol, acetonitrile), and then methanesulfonic acid was added at 20-60° C. to the mixture. The precipitated crystal was collected by filtration and dried to give the objective compound.

8-(3-pentylamino)-2-methyl-3-(2-chloro-4-methoxyphenyl)-6,7-dihydro-5H-cyclopenta[d]pyrazolo[1,5-a]pyrimidine as the starting material may be prepared by a method described in Scheme 2.

Scheme 2

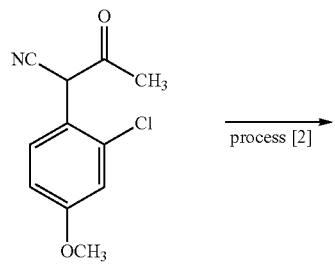

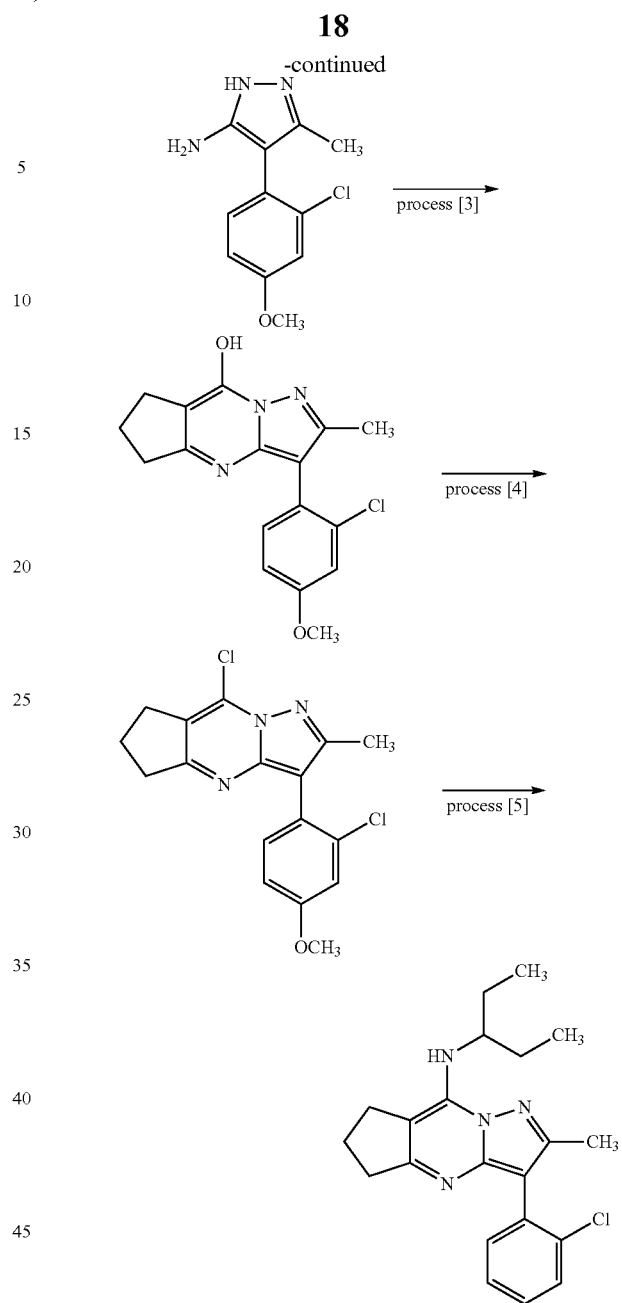

Process [2] is carried out, in an organic solvent (e.g., toluene, methanol, isopropyl alcohol, ethyl acetate, isopropyl acetate, tetrahydrofuran, acetonitrile, dimethylformamide, dimethylsulfoxide), in the presence of an acid (e.g., acetic acid, propionic acid, p-toluenesulfonic acid, methanesulfonic acid) using hydrazine, hydrazine monohydrate, or 60 to 80 wt % aqueous solution of hydrazine or hydrazine monohydrate at 10 to 60° C. or under refluxing with heat.

Process [3] is carried out, using an acid (e.g., acetic acid, sulfuric acid, methanesulfonic acid) as a solvent at 50-100° C. or under refluxing with heat, or in an organic solvent (e.g., methanol, ethanol, toluene, dimethylformamide, 1-propanol, 2-propanol, acetonitrile), in the presence of an acid (e.g., acetic acid, sulfuric acid, methanesulfonic acid, tosylic acid) at 50 to 100° C. or under refluxing with heat.

In the above reaction using an organic solvent, the amount of the acid used was smaller than the amount of the acid used as a solvent. Therefore it is easy to remove it and it is possible to carry out the reaction safely.

Process [4] is carried out, in an organic solvent (e.g., toluene, 1,2-dimethoxyethane, acetonitrile, tetrahydrofuran), in the presence of a base (e.g., pyridine, triethylamine, dimethylaniline, dimethylaminopyridine, diisopropylethylamine, 2,6-lutidine, 2-picoline, N-methylmorpholine, N-ethylmorpholine, tri-n-propylamine, tri-n-butylamine) using phosphoryl chloride at 70 to 120° C.

Process [5] is carried out, in an organic solvent (e.g., toluene, xylene, 1,2-dimethoxyethane, dimethylformamide, dimethylamine, dimethylsulfoxide, 2-propanol, acetonitrile) or without a solvent, in the presence or absence of a base (e.g., triethylamine, trimethylamine, diisopropylethylamine, N-methylmorpholine, N-ethylmorpholine, tri-n-propylamine, tri-n-butylamine) at 80 to 150° C.

In the case using methanesulfonic acid in the present invention, only the acid may be used, or it may be dissolved in an organic solvent (e.g., ethyl acetate, methanol, tetrahydrofuran, 1,2-dimethoxyethane, isopropyl alcohol, acetonitrile, n-heptane) and dropped, so that security is ensured. Methanesulfonic acid is highly caustic, and requires attention for the operation.

The quantity consumed of methanesulfonic acid is 0.5 to 2.2 equivalent, preferably 0.95 to 1.2 equivalent, to 8-(3-pentylamino)-2-methyl-3-(2-chloro-4-methoxyphenyl)-6,7-dihydro-5H-cyclopenta[d]pyrazolo[1,5-a]pyrimidine.

After methanesulfonic acid is added, an organic solvent (e.g., ethyl acetate, n-heptane) may be added and stirred to obtain the above crystal.

Compound (1) of the present invention may be purified by recrystallization using at least one of lower alcohol solvents which may contain water and ester series solvents; or a mixed solvent of one or more of the above solvents and at least one of straight-chain alkane series solvents which may contain water, esters series solvents, chained ether series solvents and ketone series solvents.

In the present invention, lower alcohol solvents means C1-4 alkane solvents having hydroxyl in the structure. Concretely, methanol, ethanol and 2-propanol are given as examples.

In the present invention, ester series solvents means solvents having an ester bond in the structure. Concretely, ethyl acetate is given as an example.

In the present invention, straight-chain alkane series solvents means solvents having a straight-chain alkane in the structure. Concretely, n-pentane, n-hexane and n-heptane are given as examples.

In the present invention, chained ether series solvents means solvents having an ether bond in the structure and the structure is a chain. The carbon substitute of an ether bond may be a chain or circular. Concretely, 1,2-dimethoxyethane, cyclopentyl methyl ether, diethyl ether, isopropyl ether and methyl-t-butyl ether are given as examples.

In the present invention, ketone series solvents means solvents having a ketone group in the structure. Concretely, acetone, etc., is given as an example.

The preferable quantity consumed of solvents in recrystallization is about 1 to 100 mL, more preferably about 2 to 50 mL, and especially preferably about 5 to 20 mL, for 1 g of the compound (1).

The solvents used for the recrystallization may contain water. The water content depends on each solvent, for example, it is from zero to a saturated amount of each solvent. Concretely, in the case of ethyl acetate, the water content is 0 to 3.3%.

The crystal may be dried at normal temperature, with warming or heating, according to need, under reduced pressure or normal pressure.

In each step of the present invention, the reaction with heating may be carried out using a water-bath, an oil-bath, a sand-bath or a microwave as will be understood by the skilled person.

In each reaction of the present invention, reaction products may be purified by a conventional purification method, for example, by distillation at a normal or reduced pressure, high performance liquid chromatography using silica gel or magnesium silicate, thin layer chromatography, ion-exchange resin, scavenger resin, column chromatography, washing or recrystallization. Purification may be done after each reaction or after several reactions.

BEST MODE FOR CARRYING OUT THE INVENTION

The following examples illustrate, but do not limit the present invention.

Example 1

1-cyano-1-(2-chloro-4-methoxyphenyl)propan-2-on

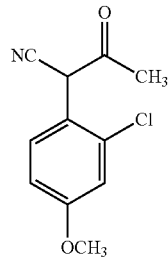

Under argon gas atmosphere, to a suspension of 1-bromo-2-chloro-4-methoxybenzene (54 g), sodium cyano acetone (28.2 g) and sodium t-butoxide (51.5 g) in 1,2-dimethoxyethane (243 mL), tetrakis(triphenylphosphine)palladium (7.04 g) was added. The mixture was refluxed with heating for 10.5 hours. The reaction mixture was cooled to 25° C., and toluene (21.6 mL) was added. The mixture was stirred for 1 hour at 20 to 30° C. of internal temperature. The reaction mixture was filtrated, and the obtained solid was washed with toluene. The obtained solid was dissolved in 2 mol/L mixed solvent of hydrochloride/toluene, and the mixture was separated. The title compound in the organic layer (300.7 g) was determined quantitatively using an internal reference method for HPLC.

Quantitative value: 71%;
Yield: 38.7 g;
TLC: Rf 0.29 (n-hexane:ethyl acetate=3:1);
NMR (300 MHz, CDCl$_3$): δ 7.38 (d, J=8.4 Hz, 1H), 7.01 (d, J=2.7 Hz, 1H), 6.90 (dd, J=8.4, 2.7 Hz, 1H), 5.12 (s, 1H), 3.83 (s, 3H), 2.29 (s, 3H).

Example 2

1-cyano-1-(2-chloro-4-methoxyphenyl)propan-2-on

Under argon gas atmosphere, to a solution of 1-bromo-2-chloro-4-methoxybenzene (120 g) in a mixed diglyme (230 mL) and 1,2-dimethoxyethane (90 mL), sodium cyano acetone (62.6 g), sodium t-butoxide (114.6 g) and sodium iodide (81.2 g) were added with stirring at room temperature to obtain a suspension. By another process, under argon gas atmosphere, a mixture of diglyme (40 mL), palladium acetate (426 mg) and triphenylphosphine (1.99 g) was stirred for about 30 minutes at 110° C. to dissolve. This solution was dropped into the above suspension. The mixture was warmed to 110 to 115° C. of internal temperature and stirred for 7 hours. The reaction mixture was cooled, diluted with ethyl acetate (480 mL) and washed with an aqueous solution of sulfuric acid (concentrated sulfuric acid 101 g/water 660 mL). The organic layer was washed with 10% saturated aqueous solution of sodium chloride (360 mL) twice. Activated charcoal (3.6 g) was added to the organic layer. The mixture was stirred for 1 hour and filtered. The filtrate was washed with ethyl acetate (240 mL) to obtain a solution of 1-cyano-1-(2-chloro-4-methoxyphenyl)propan-2-on (971.7 g).

The yield of the title compound determined using an internal reference method for HPLC described in Example 1, is 101.7 g.

Example 3

5-amino-3-methyl-4-(2-chloro-4-methoxyphenyl) pyrazole

Under argon gas atmosphere, to a solution of the compound prepared in Example 1 (38.7 g) in toluene, acetic acid (14.5 mL) and 60% aqueous solution of hydrazine hydrate (17.7 mL) were sequentially added at 10 to 30° C. of internal temperature. The mixture was stirred for 7 hours at 45 to 55° C. of internal temperature. To the reaction solution cooled to 10 to 30° C. of internal temperature, 2 mol/L hydrochloric acid was added and then the mixture was separated. The aqueous layer was adjusted to pH 6.5 to 7.5 by adding 25 wt % sodium hydroxide. Isopropyl acetate (216 mL) was added to the adjusted aqueous layer. The separated organic layer was concentrated under reduced pressure. The residue was heated, and n-heptane was added. The solution was cooled to 10 to 30° C. of internal temperature. After the crystal was precipitated, the solution was stirred for 30 minutes. Furthermore, n-heptane was added to the solution, and the mixture was stirred for 1 hour. The precipitated crystal was collected by filtration, dried under reduced pressure for 14 hours or more at about 50° C. to give the title compound having the following physical data (35.5 g (94.8 area %); quantitative value: 61% (2 processes)).

TLC: Rf 0.34 (chloroform:methanol=10:1);
NMR (300 MHz, CDCl$_3$): δ 7.19 (d, J=8.1 Hz, 1H), 7.04 (d, J=2.7 Hz, 1H), 6.86 (dd, J=8.1, 2.7 Hz, 1H), 3.83 (s, 3H), 2.14 (s, 3H).

Example 4

8-hydroxy-2-methyl-3-(2-chloro-4-methoxyphenyl)-6,7-dihydro-5H-cyclopenta[d]pyrazolo[1,5-a]pyrimidine Under argon gas atmosphere, to a solution of the compound prepared in Example 3 (26.0 g) in ethanol (109 mL), 2-oxocyclopentanecarboxylic acid ethyl ester (17.3 mL) was added at 10 to 30° C. of internal temperature, and acetic acid (18.7 mL) was added. The mixture was refluxed with heating for 7 hours at 80 to 90° C. of internal temperature. After the reaction mixture was cooled to 55 to 65° C. of internal temperature, toluene (109 ml) was added. The diluted solution was stirred for 30 minutes or more at 40 to 65° C. of internal temperature, and then the solution was cooled to 10 to 30° C. The precipitated crystal was collected by filtration, dried under reduced pressure for 14 hours or more at about 50° C. to give the title compound having the following physical data (33.3 g (98.6 area %); quantitative value: 92.8%).

TLC: Rf 0.59 (chloroform:methanol:acetic acid:water=50:10:1:1);
NMR (300 MHz, DMSO-d$_6$): δ 12.04 (s, 1H), 7.31 (d, J=8.4 Hz, 1H), 7.18 (d, J=2.4 Hz, 1H), 7.00 (dd, J=8.4, 2.4 Hz, 1H), 3.81 (s, 3H), 2.82 (t, J=7.5 Hz, 2H), 2.66 (t, J=6.9 Hz, 2H), 2.11 (s, 3H), 2.03 (m, 2H).

Example 5

8-chloro-2-methyl-3-(2-chloro-4-methoxyphenyl)-6,7-dihydro-5H-cyclopenta[d]pyrazolo[1,5-a]pyrimidine Under argon gas atmosphere, to a suspension of the compound prepared in Example 4 (300 g) in toluene (910 mL), N,N-diisopropylethylamine (141 g) was added, and then phosphoryl chloride (419 g) was dropped. The mixture was stirred for 9 hours at 80 to 95° C. of internal temperature. The reaction solution cooled to 20 to 30° C. of internal temperature was poured into a mixed solvent of ethyl acetate and water, and the mixture was stirred for 15 minutes. The organic layer was washed with a saturated aqueous solution of sodium bicarbonate and a saturated aqueous solution of sodium chloride, then activated charcoal (30 g) was added, followed by stirring for 1 hour, and the mixture was filtered. N,N-Dimethylacetamide (600 mL) was added to the filtrate. The mixture was concentrated under reduced pressure. The solution of the title compound (316.9 g; 100% conversion) having the following physical data in N,N-dimethylacetamide was used in the next step without purification.

TLC: Rf 0.42 (n-hexane:ethyl acetate=2:1);
NMR (300 MHz, CDCl$_3$): δ 7.28 (d, J=8.7 Hz, 1H), 7.07 (d, J=2.4 Hz, 1H), 6.90 (dd, J=8.7, 2.4 Hz, 1H), 3.84 (s, 3H), 3.06 (m, 4H), 2.43 (s, 3H), 2.23 (m, 2H).

Example 6

8-(3-pentylamino)-2-methyl-3-(2-chloro-4-methoxyphenyl)-6,7-dihydro-5H-cyclopenta[d]pyrazolo[1,5-a]pyrimidine Under argon gas atmosphere, a mixture of a solution of the compound prepared in Example 5 (177.6 g) in N,N-dimethylacetamide (355 mL) and a solution of triethylamine (103.2 g) and 3-aminopentane (88.9 g) in isopropyl alcohol (178 mL) was stirred for 4 hours at 95 to 105° C. of internal temperature. Water was poured into the reaction solution that was cooled to 70 to 80° C. of internal temperature. The diluted solution was cooled to 50 to 60° C. of internal temperature, and then after the crystal was precipitated, the solution was stirred for 30 minutes. Furthermore, water was poured into the solution, and the diluted solution was stirred for 1 hour at 20 to 30° C. of internal temperature. The precipitated crystal was collected by filtration, and the obtained crystal was dried under reduced pressure for 14 hours or more at about 50° C. to give the crude crystal of the title compound (174 g, (97.4 area %), quantitative value: 85% (two process)).

A solution of the obtained crude crystal (1.0 g) in ethanol/water (3/1; 2 mL) was refluxed with heating in oil-bath. Furthermore, ethanol/water (3/1; 5 mL) was added. Oil-bath was removed and the solution was allowed to stand overnight.

The precipitated crystal was collected by filtration, and washed with ethanol/water (3/1), and dried under reduced pressure for 14 hours or more at about 50° C. to give the title compound (920 mg) having the following physical data.

TLC: Rf 0.45 (n-hexane:ethyl acetate=2:1);

NMR (300 MHz, CDCl$_3$): δ 7.31 (d, J=8.4 Hz, 1H), 7.05 (d, J=2.7 Hz, 1H), 6.88 (dd, J=8.4, 2.7 Hz, 1H), 6.22 (brd, J=10.5 Hz, 1H), 3.82 (s, 3H), 3.80 (m, 1H), 3.08 (t, J=7.2 Hz, 2H), 2.90 (t, J=7.5 Hz, 2H), 2.34 (s, 3H), 2.14 (m, 2H), 1.52-1.82 (m, 4H), 1.01 (t, J=7.5 Hz, 3H).

Example 7

8-(3-pentylamino)-2-methyl-3-(2-chloro-4-methoxyphenyl)-6,7-dihydro-5H-cyclopenta[d]pyrazolo[1,5-a]pyrimidine methanesulfonate

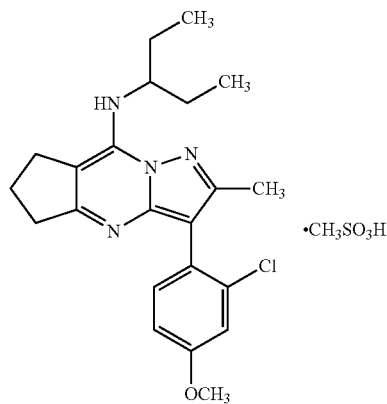

The crude crystal prepared in Example 6 (71.6 g) was dissolved in ethyl acetate (250 mL) with heating. After the solution was cooled to 50° C. of internal temperature, 99.3% methanesulfonic acid (17.3 g) was dropped into the solution. To the mixed solution cooled to 30° C. of internal temperature, n-heptane was added, and then the mixture was stirred for 30 minutes at 25° C. The obtained crystal was collected by filtration, and dried under reduced pressure for 14 hours or more at about 50° C. to the title compound (87.1 g (97.4 area %); quantitative value: 98%) as powdered crystal.

TLC: Rf 0.17 (n-hexane:ethyl acetate=2:1);

Melting point: 196-197° C. (non-correction, heated metal block);

NMR (300 MHz, CDCl$_3$): δ 7.36 (d, J=8.4 Hz, 1H), 7.23 (d, J=10.5 Hz, 1H), 7.08 (d, J=2.4 Hz, 1H), 6.97 (dd, J=8.4, 2.4 Hz, 1H), 4.03-3.90 (m, 1H), 3.85 (s, 3H), 3.63-3.35 (m, 2H), 3.13 (t, J=7.2 Hz, 2H), 2.42 (s, 3H), 2.35-2.25 (m) and 2.34 (s) total 5H, 1.90-1.50 (m, 4H), 1.06 (t, J=7.5 Hz) and 1.05 (t, J=7.5 Hz) total 6H.

Physical Properties Data of the Crystal

X-ray powder diffraction spectrum, IR spectrum and DSC chart of the compound prepared in Example 7 measured under the terms and conditions stated below were shown in FIG. 3, FIG. 4 and FIG. 1, respectively.

(1) X-Ray Powder Diffraction Spectrum

| Apparatus: | BRUKER DISCOVER with GADD(C2) produced by BRUKER, |
|---|---|
| Target: | Cu, |
| Filter: | none, |
| Voltage: | 40 kV, |
| Electrical current: | 40 mA, |
| Exposure time: | 5 min. |

(2) Infrared Resonance (IR) Spectrum

| Apparatus: | FTIR-660Plus produced by JASCO Corporation/DURASCOPE produced by SENSIR, |
|---|---|
| Measuring method: | crystal was measured by ATR method, |
| Dissolution performance: | 4 cm$^{-1}$, |
| Scanning number of times: | 16 times. |

(3) Differential Scanning Calorimeter (DSC)

| Apparatus: | SEIKO INSTRUMENT DSC6200, |
|---|---|
| Sample quantity: | 6.35 mg, |
| Sample cell: | aluminum open cell, |
| Nitrogen gas flow: | 20 mL/min, |
| Heating rate: | 5° C./min. |

Example 7(1)

The compound prepared in Example 7 (500 mg) was put into screw pipe (18 mm across, 40 mm high), and then methanol (0.5 mL) and ethyl acetate (0.5 mL) were added. After closing the lid, the screw pipe was heated in oil-bath. After the solid was dissolved, the mixture was allowed to cool under light shielding and room temperature, and single-crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate was obtained.

Figure 5:
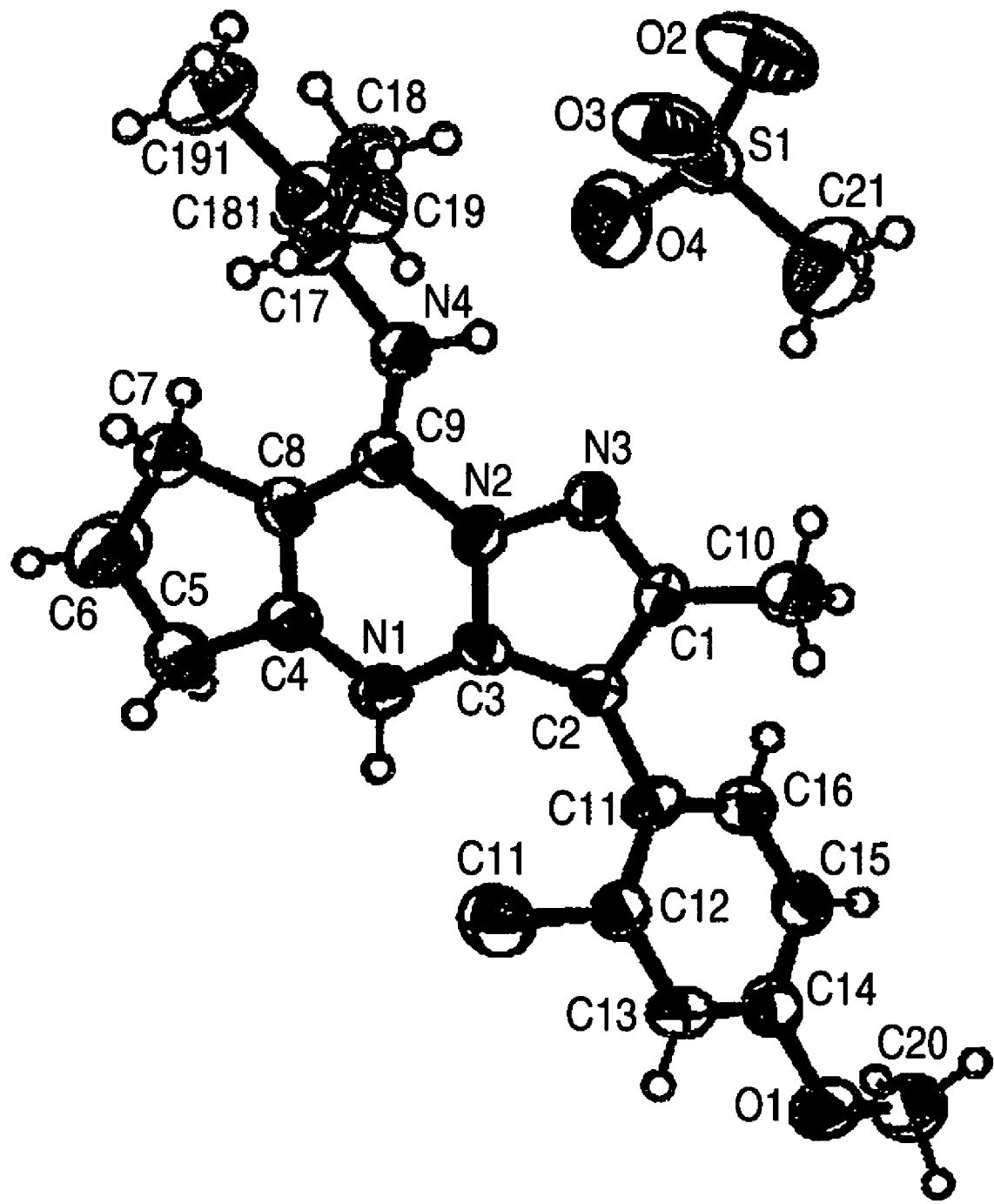
FIG. 5 shows X-ray structural analysis data of single-crystal of the compound 1.
Figure 6:
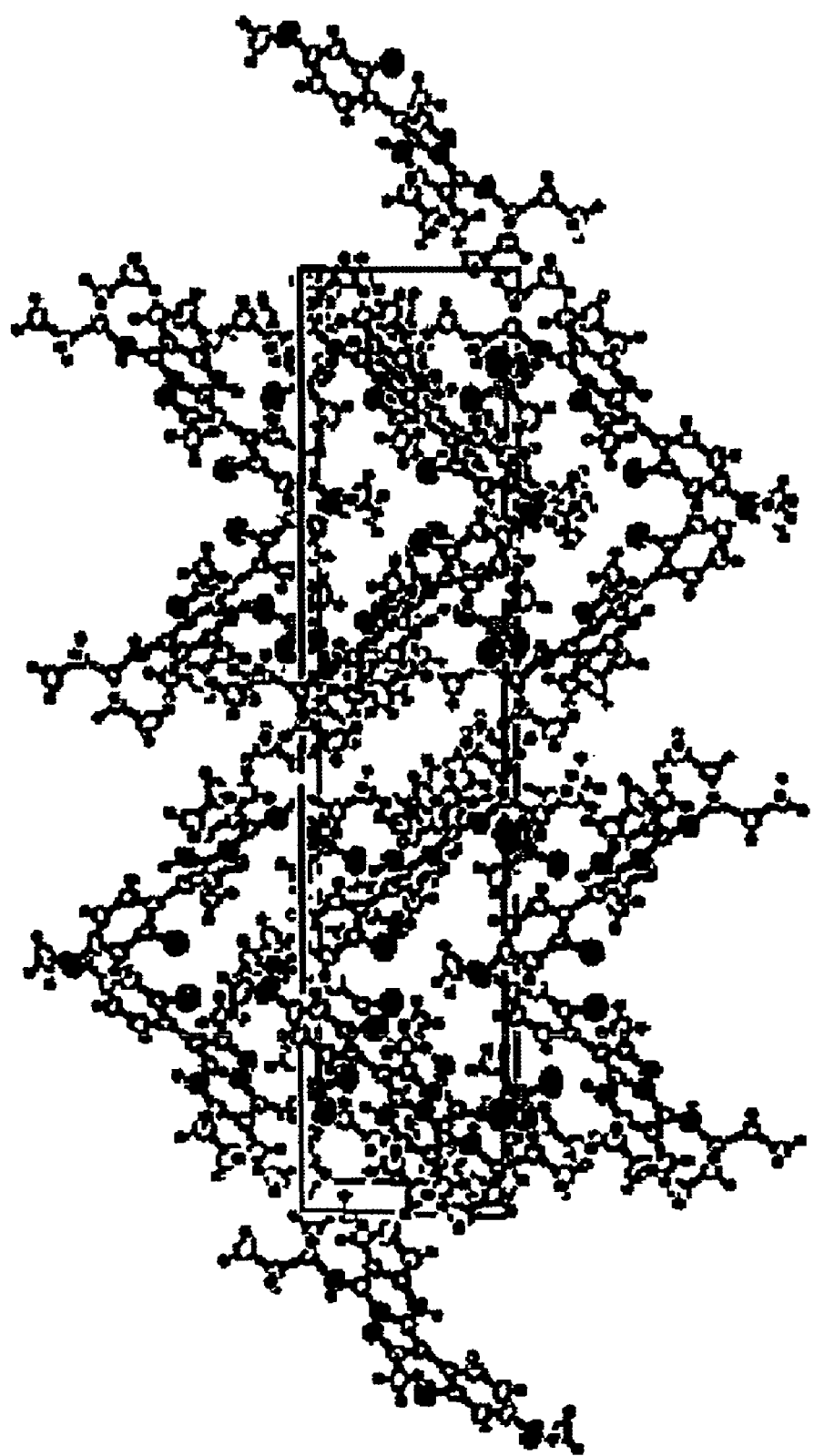
FIG. 6 shows X-ray structural analysis data of single-crystal of the compound 1.

Single-crystal X-ray structural analysis data of the compound (1) were shown ins FIG. 5 and FIG. 6.
Measurement Condition

| Apparatus: | R-AXIS RAPID type of single-crystal X-ray structural analysis appliance produced by Rigaku Co., |
|---|---|
| Analysis software: | Crystal Structure produced by Rigaku Co., |
| Measurement temperature: | room temperature, |
| Target: | CuKα (λ = 1.54187 Å), R = 0.059. |

Crystallographic data were shown as follows.

| Lattice constant: | a = 8.165(2)Å, b = 38.140(8)Å, c = 7.947(2)Å, β = 94.32(2)°, |
|---|---|
| Space group: | P2$_{1/c}$ |

Example 8

8-(3-pentylamino)-2-methyl-3-(2-chloro-4-methoxyphenyl)-6,7-dihydro-5H-cyclopenta[d]pyrazolo[1,5-a]pyrimidine tosylate The crude crystal prepared in Example 6 (100 mg) was dissolved into tetrahydrofuran (0.5 mL) with heating. The mixture was cooled to 60° C., and tosylic acid (47.7 mg) was added to the mixture. The mixture was cooled to 25° C., and methyl t-butyl ether (2.5 mL) was added. The precipitated crystal was collected by filtration. The obtained crystal was dried over 14 hour or more under reduce pressure at 50° C. to give the title compound (105 mg, (97.6 area %); quantitative value: 71.1%) having the following physical data as powder crystal.

TLC: Rf 0.38 (n-hexane:ethyl acetate=2:1);

NMR (200 MHz, CDCl$_3$): δ 7.51 (d, J=8.4 Hz, 2H), 7.31 (d, J=8.6 Hz, 1H), 7.30-7.20 (m, 1H), 7.09 (d, J=8.4 Hz, 2H), 6.93 (d, J=2.6 Hz, 1H), 6.69 (dd, J=8.6, 2.6 Hz, 1H), 4.10-3.90 (m, 1H), 3.80-3.35 (m) and 3.72 (s) total 5H, 3.14 (t, J=7.2 Hz, 2H), 2.40-2.20 (m, 2H), 2.35 (s, 3H), 2.33 (s, 3H), 1.90-1.60 (m, 4H), 1.06 (t, J=7.5 Hz) and 1.05 (t, J=7.5 Hz) total 6H.

Pharmacological Activities

It was confirmed that compound (1) possesses the CRF receptor antagonistic activity by the following experiments.

Experiment 1
Binding Assay:
Cell Membrane Preparation

After a cell line expressing a human CRF1 receptor (expressed cell line: CHO-K1 cells) was cultured to reach confluence, the cells were harvested with a scraper. Harvested cells were washed twice with PBS before being suspended in a binding assay buffer (Tris-HCl (50 mM, pH 7.0), EDTA (2 mM, pH 8.0), and MgCl$_2$ (10 mM)) cooled by ice. Suspended cells were homogenized with a Downs-type homogenizer and subjected to centrifugation at 10,000 g to collect the membrane fraction. The harvested cell membrane fraction was re-suspended with a small quantity of the binding assay buffer, and further diluted with said buffer to 1 mg/mL. The membrane fraction thus obtained was used for binding assay.

Binding Assay

Fifty μL of [$^{125}$I] h/r CRF prepared to 0.5 nM with binding assay buffer was added to siliconized 1.5 mL tubes. Each of 1 μL of compounds diluted in appropriate multiples, DMSO (for total binding use) and h/r CRF solution (100 μM, for the non-specific binding use) was added to the tubes. Samples of 50 μL each of the membrane fraction preparation were added to the tubes to initiate the reaction (final concentration of [$^{125}$I] h/r CRF: 0.25 nM), then the mixtures were incubated for 2 hours at room temperature. After termination of the reaction, the tubes were subjected to centrifugation at 20,000 g to collect the membrane fraction. The supernatant was discarded, and the pellet was rinsed twice with cooled PBS (−) containing 0.01% Triton X-100. Radioactivity values of the respective tubes were measured with a γ-counter.

The specific binding was derived by subtracting the non-specific binding value from the each binding value.

The results indicated that compound (1) exhibited potent affinity on CRF1 receptor (IC$_{50}$: <1 μM).

Experiment 2
Receptor Antagonistic Activity (Cyclic AMP Assay):

A cell line expressing a human CRF1 receptor was cultured using 10% bovine embryo serum and 1% F-12 nutrient mixture containing antibiotics and antifungal under 37° C., 5% carbonic anhydride, 95% air. On the day before a measurement of cyclic AMP, the cell seed to 96-well plate to be 1×10$^4$ cell/well. On the measurement day, the cell was washed twice with F-12 nutrient mixture, and F-12 nutrient mixture/1 mM 3-isobutyl-1-methylxanthin (assay medium) (178 μL) was added to each well. After they were incubated for 10 minutes at 37° C., each of various concentrated solutions of the test compound (2 μL) was added, or DMSO (2 μL) was added to CRF group and blank group. After they were incubated for 15 minutes at 37° C., 10 nM assay medium containing human/rat CRF (20 μL) was added to the test compound group and CRF group. To the blank group, an assay medium containing 0.00001% acetic acid (20 μL) was added. Furthermore, they were incubated for 15 minutes at 37° C. A supernatant was removed, and the reaction was stopped by cooling using ice. Also, all reaction was carried out by 3 wells. The cumulative dosage of intracellular cyclic AMP was measured by Biotrak enzyme immunoassay system (Amersham Biosciences). The cumulative dosage of cyclic AMP was derived by subtracting the average value of 3 wells of blank group from the average value of 3 wells. The IC$_{50}$ values calculated by nonlinear regression analysis with logarithm concentrate of the compound as the autonomous variable and cyclic AMP cumulative dosage as an induced variable The results indicated that compound (1) exhibited potent antagonist activity on CRF receptor (IC$_{50}$: <1 μM).

Formulation Example 1

The following components were admixed in a conventional method and punched out to obtain one million tablets each containing 10 mg of the active ingredient.

| | |
|---|---|
| 8-(3-Pentylamino)-2-methyl-3-(2-chloro-4-methoxyphenyl)-6, 7-dihydro-5H-cyclopenta[d]pyrazolo[1,5-a]pyrimidine methanesulfonate | 10 kg |
| Carboxymethylcellulose calcium (disintegrating agent) | 2 kg |
| Magnesium stearate (lubricating agent) | 1 kg |
| Microcrystalline cellulose | 87 kg |

Formulation Example 2

The following components were admixed in a conventional method. The solution was sterilized in conventional manner, placed 5 ml portions into ampoules and freeze-dried to obtain one million ampoules each containing 20 mg of the active ingredient.

| | |
|---|---|
| 8-(3-Pentylamino)-2-methyl-3-(2-chloro-4-methoxyphenyl)-6, 7-dihydro-5H-cyclopenta[d]pyrazolo[1,5-a]pyrimidine methanesulfonate | 20 kg |
| Mannitol | 200 kg |
| Distilled water | 5 kl |
| 1N Hydrochloric acid | 20 to 30 ml |

The invention claimed is:

1. A crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate, which has X-ray powder diffraction spectrum shown in FIG. 3.

2. A crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate, which has diffraction angle 2θ at 8.96, 12.70, 13.69, 14.98, 15.74, 16.38, 17.63, 18.98, 19.71, 20.49, 21.37, 22.26, 22.88, 23.76, 24.70, 25.79 and 26.57 on X-ray powder diffraction spectrum.

3. A crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate, which has infrared resonance spectrum shown in FIG. 4.

4. A crystal of 8-(3-pentylamino)-2-methyl-3-(2-chloro-4-methoxyphenyl)-6,7-dihydro-5H-cyclopenta[d]pyrazolo[1,5-a]pyrimidine methanesulfonate, which has absorption of infrared resonance spectrum at 1652, 1595, 1549, 1220, 1168, 1141, 1115, 1034, 790, 766, 548, 533 and 522 cm$^{-1}$.

* * * * *